(12) United States Patent
Richardson et al.

(10) Patent No.: US 8,642,548 B2
(45) Date of Patent: Feb. 4, 2014

(54) VAL (8) GLP-1 COMPOSITION AND METHOD FOR TREATING FUNCTIONAL DYSPEPSIA AND/OR IRRITABLE BOWEL SYNDROME

(75) Inventors: Peter Richardson, Ringoes, NJ (US); Enda Kenny, Killiney (IE); Per Hellstrom, Bromma (SE); Marshall L. Grant, Newtown, CT (US); Grayson W. Stowell, Gaylordsville, CT (US); Scott Daniels, Cheshire, CT (US); Anthony Smithson, Santa Clarita, CA (US); Stephanie Greene, Ventura, CA (US)

(73) Assignee: Mannkind Corporation, Valencia, CA (US)

( * ) Notice: Subject to any disclaimer, the term of this patent is extended or adjusted under 35 U.S.C. 154(b) by 0 days.

(21) Appl. No.: 13/389,410

(22) PCT Filed: Aug. 5, 2010

(86) PCT No.: PCT/US2010/044600
§ 371 (c)(1),
(2), (4) Date: Feb. 7, 2012

(87) PCT Pub. No.: WO2011/017554
PCT Pub. Date: Feb. 10, 2011

(65) Prior Publication Data
US 2012/0252728 A1    Oct. 4, 2012

Related U.S. Application Data

(60) Provisional application No. 61/232,373, filed on Aug. 7, 2009, provisional application No. 61/232,380, filed on Aug. 7, 2009.

(51) Int. Cl.
*A61K 38/26*   (2006.01)
*A61P 3/10*    (2006.01)
*A61P 7/12*    (2006.01)
*C07K 14/605*  (2006.01)

(52) U.S. Cl.
USPC ............................................. 514/11.7

(58) Field of Classification Search
None
See application file for complete search history.

(56) References Cited

U.S. PATENT DOCUMENTS

| | | | |
|---|---|---|---|
| 5,118,666 A | 6/1992 | Habener | |
| 6,071,497 A | 6/2000 | Steiner et al. | |
| 6,380,357 B2 * | 4/2002 | Hermeling et al. | 530/324 |
| 6,428,771 B1 | 8/2002 | Steiner et al. | |
| 6,444,226 B1 | 9/2002 | Steiner | |
| 2003/0060412 A1 * | 3/2003 | Prouty et al. | 514/12 |
| 2004/0038865 A1 | 2/2004 | Gelber et al. | |
| 2004/0096403 A1 | 5/2004 | Steiner | |
| 2005/0043228 A1 * | 2/2005 | DeFelippis et al. | 514/12 |
| 2006/0239933 A1 | 10/2006 | Nilsson | |

FOREIGN PATENT DOCUMENTS

| | | |
|---|---|---|
| WO | 93/18754 A1 | 9/1993 |
| WO | 01/00654 A2 | 1/2001 |
| WO | 02/11676 | 2/2002 |
| WO | 02/098348 A2 | 12/2002 |
| WO | 2006/023943 A1 | 3/2006 |
| WO | 2007/033316 A2 | 3/2007 |
| WO | 2007/121411 A2 | 10/2007 |
| WO | WO 2007121411 A2 * | 10/2007 |
| WO | 2009/055740 A2 | 4/2009 |

OTHER PUBLICATIONS

Weissberger, "Mannkind: Overlooked Biotech With Excellent Prospects (Part V)" http://www.investorvillage.com/smbd.asp?mb=2885& mn=45817&pt=msg&mid=5021385 (posted on Jun. 19, 2008, accessed on Oct. 18, 2012).*
International Preliminary Report on Patentability, Application No. PCT/US2010/038298 mailed Apr. 3, 2012.
European Search Report, Application No. 11180288.0 dated Dec. 22, 2011.
AU Examiners Report, Application No. 2007238000, mailed Mar. 22, 2012.
CN Office Action cited in Application No. 200880122670.3 mailed on Nov. 23, 2011.
Hui et al., "The short half-life of glucagon-like peptide-1 in plasma does not reflect its long-lasting beneficial effects", European Journal of Endocrinology (2002), 146 : 863-869.
Glucagon-like peptide-1, http://en.wikipedia.org/wiki/Glucagon-like peptide-1.
Akerlund et al., Diketopiperazine-Based Polymers from Common Amino Acids. Journal of Applied Polymer Science, vol. 78, 2213-2218 (2000).
Li, Jun. Chapter 15: Drug Therapy of Metabolic Diseases. Clinical Pharmacotherapy, People's Medical Publishing House, 1st. Edition, pp. 333-335 (2007).

* cited by examiner

*Primary Examiner* — Marcela M Cordero Garcia
*Assistant Examiner* — Kaipeen Yang
(74) *Attorney, Agent, or Firm* — K&L Gates LLP; Louis C. Cullman; Hal Gibson

(57) ABSTRACT

A method of treating functional dyspepsia and/or irritable bowel syndrome in mammals in need of treatment is disclosed herein. The method comprises administering to the mammal a formulation by inhalation, wherein the formulation avoids first pass metabolism of the active ingredient. The method comprises administering a formulation by pulmonary inhalation comprising a diketopiperazine and a glucagon-like peptide (GLP-1), analog, ROSE-010.

19 Claims, 7 Drawing Sheets

```
                           SEQUENCE LISTING

<160> NUMBER OF SEQ ID NOS: 3

<210> SEQ ID NO 1
<211> LENGTH: 31
<212> TYPE: PRT
<213> ORGANISM: homo sapiens

<400> SEQUENCE: 1

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 37
<212> TYPE: PRT
<213> ORGANISM: homo sapiens

<400> SEQUENCE: 2

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 3
<211> LENGTH: 31
<212> TYPE: PRT
<213> ORGANISM: homo sapiens
<220> FEATURE:
<221> NAME/KEY: VARIANT
<222> LOCATION: (1)..(1)
<223> OTHER INFORMATION: Xaa = L-histidine, D-histidine,
      desaminohistidine, 2-amino-histidine, beta-hydroxy-histidine,
      homohistidine, alpha-fluoromethylhistidine, or
      alpha-methyl-histidine
<220> FEATURE:
<221> NAME/KEY: VARIANT
<222> LOCATION: (2)..(2)
<223> OTHER INFORMATION: Xaa = Ala, Gly, Val, Thr, Ile, or
      alpha-methyl-Ala
<220> FEATURE:
<221> NAME/KEY: VARIANT
<222> LOCATION: (15)..(15)
<223> OTHER INFORMATION: Xaa = Glu, Gln, Ala, Thr, Ser, or Gly
<220> FEATURE:
<221> NAME/KEY: VARIANT
<222> LOCATION: (21)..(21)
<223> OTHER INFORMATION: Xaa = Glu, Gln, Ala, Thr, Ser, or Gly
<220> FEATURE:
<221> NAME/KEY: VARIANT
<222> LOCATION: (31)..(31)
<223> OTHER INFORMATION: Xaa = Gly-NH2 or Gly-OH

<400> SEQUENCE: 3

Xaa Xaa Glu Gly Thr Phe Thr Ser Asp Val Ser Ser Tyr Leu Xaa Gly
1               5                   10                  15

Gln Ala Ala Lys Xaa Phe Ile Ala Trp Leu Val Lys Gly Arg Xaa
            20                  25                  30
```

VAL (8) GLP-1 COMPOSITION AND METHOD FOR TREATING FUNCTIONAL DYSPEPSIA AND/OR IRRITABLE BOWEL SYNDROME

CROSS REFERENCE TO RELATED APPLICATIONS

This application claims benefit of priority under 35 U.S.C §119(e) from U.S. Provisional Applications Ser. Nos. 61/232,373 and 61/232,380, both filed on Aug. 7, 2009, which disclosures are hereby incorporated by reference in their entirety.

TECHNICAL FIELD

A composition and method of treating functional dyspepsia and/or irritable bowel syndrome in a mammal is disclosed herein. The composition comprising a diketopiperazine and a glucagon-like peptide 1 (GLP-1), a GLP-1 analog, including the analog ROSE-010 (Val (8) GLP-1), or a combination thereof. The method further comprises administering to the mammal a GLP-1 formulation by inhalation.

BACKGROUND

Drug delivery systems for the treatment of disease which introduce active ingredients into the circulation are numerous and include oral, transdermal, subcutaneous and intravenous administration. While these systems have been used for quite a long time and can deliver sufficient medication for the treatment of many diseases, there are numerous challenges associated with these drug delivery mechanisms. In particular, delivery of effective amounts of proteins and peptides to treat a target disease has been problematic. Many factors are involved in introducing the right amount of the active agent, for example, preparation of the proper drug delivery formulation so that the formulation contains an amount of active agent that can reach its site(s) of action in an effective amount.

The active agent must be stable in the drug delivery formulation and the formulation should allow for absorption of the active agent into the circulation and remain active so that it can reach the site(s) of action at effective therapeutic levels. Thus, in the pharmacological arts, drug delivery systems which can deliver a stable active agent are of utmost importance.

Making drug delivery formulations therapeutically suitable for treating disease depends on the characteristics of the active ingredient or agent to be delivered to the patient. Such characteristics can include, in a non-limiting manner, solubility, pH, stability, toxicity, release rate, and ease of removal from the body by normal physiologic processes. For example, in oral administration, if the agent is sensitive to acid, enteric coatings have been developed using pharmaceutically acceptable materials which can prevent the active agent from being released in the low pH (acid) of the stomach. Thus, polymers that are not soluble at acidic pH are used to formulate and deliver a dose containing acid-sensitive agents to the small intestine where the pH is neutral. At neutral pH, the polymeric coating can dissolve to release the active agent which is then absorbed into the systemic circulation. Orally administered active agents enter the systemic circulation and pass through the liver. In certain cases, some portion of the dose is metabolized and/or deactivated in the liver before reaching the target tissues. In some instances, the metabolites can be toxic to the patient, or can yield unwanted side effects.

Similarly, subcutaneous and intravenous administrations of pharmaceutically-active agents are not devoid of degradation and inactivation of the active ingredients. With intravenous administration of drugs, the drugs or active ingredients can also be metabolized, for example in the liver, before reaching the target tissue. With subcutaneous administration of certain active agents, including various proteins and peptides, there is additionally degradation and deactivation by peripheral and vascular tissue enzymes at the site of drug delivery and during travel through the venous blood stream. In order to deliver a dose that will yield an acceptable quantity for treating disease with subcutaneous and intravenous administration of an active agent, dosing regimes will always have to account for the inactivation of the active agent by peripheral and vascular venous tissue and ultimately the liver.

SUMMARY

The present disclosure relates to a pharmaceutical composition comprising GLP-1, a GLP-1 analog including the Val$^8$ glucagon-like peptide-1(7-37)OH (ROSE-010) having the following amino acid sequence:

```
                              (ROSE-010; SEQ ID NO: 1)
H-His-Val-Glu-Gly-Thr-Phe-Thr-Ser-Asp-Val-Ser-Ser-Tyr-Leu-Glu-

Gly-Gln-Ala-Ala-Lys-Glu-Phe-Ile-Ala-Trp-Leu-Val-Lys-Gly-Arg-

Gly-OH
``` wherein Val (8) GLP-1 is a truncated version of human GLP-1, and wherein human GLP-1 has the following amino acid sequence: His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO: 2). Furthermore Val (8) GLP-1 has an Ala→Val amino acid substitution at position 8 of human GLP-1.

The pharmaceutical composition further comprises a diketopiperazine. In one embodiment, the diketopiperazine is selected from the group consisting of 2,5-diketo-3,6-di(4-X-aminobutyl)piperazine; wherein X is selected from the group consisting of succinyl, glutaryl, maleyl, and fumaryl, or a pharmaceutically acceptable salt thereof.

Also disclosed is a method of treating any disease or disorder wherein GLP-1 is indicated including, but not limited to, diabetes, ischemia, reperfused tissue injury, dyslipidemia, diabetic cardiomyopathy, myocardial infarction, acute coronary syndrome, obesity, catabolic changes after surgery, hyperglycemia, irritable bowel syndrome, stroke, neurodegenerative disorders, memory and learning disorders, islet cell transplant functional dyspepsia and/or regenerative therapy in mammals in need of treatment. The method comprises administering to the mammal a formulation by pulmonary inhalation, wherein the formulation avoids first pass metabolism of the active ingredient. In one embodiment, the method of treating functional dyspepsia and/or irritable bowel syndrome in a mammal in need of treatment comprises administering to the mammal a therapeutically effective amount of a formulation by pulmonary inhalation, comprising a diketopiperazine having the formula: 3,6-bis[4-(N-carboxy-2-propenyl)amidobutyl]-2,5-diketopiperazine (fumaryl diketopiperazine, FDKP) and ROSE-010, a GLP-1 analog.

In yet another embodiment, there is provided a method for treating irritable bowel syndrome in a patient having the disease, the method comprising administering to the patient a therapeutically effective amount of a formulation by pulmonary inhalation, which formulation comprises FDKP and GLP-1 or a GLP-1 analog, such as the GLP-1 analog ROSE-010, which inhibits gastrointestinal smooth muscle motor activity and inhibits secretory activity of gastroinstestinal glands for about 6 to 8 hours after administration.

In another embodiment, the method of treating irritable bowel syndrome comprises a dry powder inhalation system comprising a cartridge containing a dry powder formulation for pulmonary delivery and a breath powered inhaler. In one aspect of this embodiment, the inhaler can be a high resistance inhaler.

In one embodiment disclosed herein, a pharmaceutical composition is provided comprising Val (8) glucagon-like peptide-1 (GLP-1) and a diketopiperazine or a pharmaceutically acceptable salt, solvate or prodrug thereof. In another embodiment, the composition is an inhalable dry powder composition.

In another embodiment, the diketopiperazine is a diketopiperazine having the formula 2,5-diketo-3,6-di(4-X-aminobutyl)piperazine, wherein X is selected from the group consisting of succinyl, glutaryl, maleyl, and fumaryl. In another embodiment, the diketopiperazine is a diketopiperazine salt. In yet another embodiment, the diketopiperazine is 2,5-diketo-3,6-di(4-fumaryl-aminobutyl)piperazine.

In another embodiment, Val (8) GLP-1 is an amidated Val (8) GLP-1.

In one embodiment disclosed herein, a process is provided for forming a particle comprising Val (8) GLP-1 and a diketopiperazine comprising the steps of: providing a Val (8) GLP-1; providing a diketopiperazine in a form selected from particle-forming diketopiperazine, diketopiperazine particles, and combinations thereof; and combining said Val (8) GLP-1 and said diketopiperazine in the form of a co-solution, wherein said particle comprising said Val (8) GLP-1 and said diketopiperazine is formed.

In another embodiment, the process further comprises removing a solvent from said co-solution by lyophilization, filtration, or spray drying. In another embodiment, the particle comprising Val (8) GLP-1 and a diketopiperazine is formed by removing solvent. In another embodiment, the particle comprising Val (8) GLP-1 and a diketopiperazine is formed prior to removing solvent.

In another embodiment, Val (8) GLP-1 is provided in the form of a solution comprising a Val (8) GLP-1 concentration of about 0.001 mg/ml-50 mg/ml. In another embodiment, the Val (8) GLP-1 concentration is about 0.1 mg/ml-10 mg/ml. In another embodiment, the Val (8) GLP-1 concentration is about 0.25 mg/ml.

In another embodiment, the diketopiperazine is provided in the form of a suspension of diketopiperazine particles. In yet another embodiment, the diketopiperazine is provided in the form of a solution comprising particle-forming diketopiperazine, the process further comprising adjusting the pH of the solution to form diketopiperazine particles. In another embodiment, the process further comprises adding an agent to the solution or suspension, wherein the agent is selected from the group consisting of salts, surfactants, ions, osmolytes, chaotropes and lyotropes, acids, bases, and organic solvents, in one embodiment, sodium chloride. In another embodiment, the agent promotes association between Val (8) GLP-1 and the diketopiperazine particles or the particle-forming diketopiperazine.

In one embodiment disclosed herein, a method is provided of administering an effective amount of a Val(8) GLP-1 to a subject in need thereof, the method comprising providing to the subject an inhalable dry powder formulation comprising Val(8) GLP-1 and diketopiperazine, in particularly wherein the administration is carried out by pulmonary delivery.

In another embodiment, the pulmonary delivery is obtained using a dry powder inhalation system. In another embodiment, the dry powder inhalation system comprises a cartridge. In yet another embodiment, the dry powder formulation further comprises a pharmaceutically acceptable carrier or excipient.

In another embodiment, the need comprises the treatment of a condition or disease selected from the group consisting of diabetes, ischemia, reperfused tissue injury, dyslipidemia, diabetic cardiomyopathy, myocardial infarction, acute coronary syndrome, obesity, catabolic changes after surgery, hyperglycemia, irritable bowel syndrome, functional dyspepsia, stroke, neurodegenerative disorders, memory and learning disorders, islet cell transplant and regenerative therapy. In another embodiment, the need comprises the treatment of irritable bowel syndrome.

In another embodiment, a dosage of from about 10 µg to about 900 µg of Val(8) GLP-1 is administered per administration, or a dosage of from about 25 µg to about 500 µg of Val(8) GLP-1 is administered per administration, or a dosage of from about 50 µg to about 300 µg of Val(8) GLP-1 is administered per administration.

In one embodiment disclosed herein, a method is provided of administering an effective amount of a GLP-1 molecule or a GLP-1 analog to a subject in need of treatment of irritable bowel syndrome, the method comprising providing to the subject an inhalable dry powder formulation comprising a GLP-1 molecule or GLP-1 analog and a diketopiperazine, wherein the administration is carried out by pulmonary delivery.

In one embodiment disclosed herein, a method is provided of forming a powder composition with an improved GLP-1 pharmacokinetic profile, comprising the steps of: providing a Val (8) GLP-1; providing a particle-forming diketopiperazine in a solution; forming diketopiperazine particles; combining the Val (8) GLP-1 and the solution to form a co-solution; and removing solvent from the co-solution by spray-drying to form a powder with an improved GLP-1 pharmacokinetic profile.

DEFINITION OF TERMS

Figure 1:
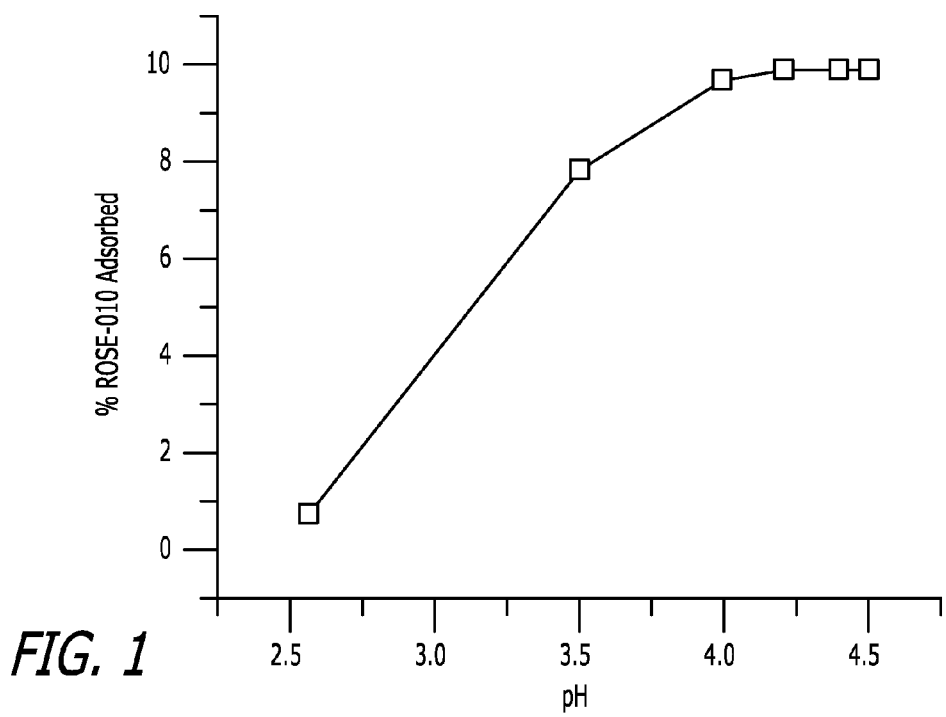
FIG. 1 depicts a graph of a GLP-1 analog, ROSE-010, adsorption onto fumaryl diketopiperazine (FDKP) particles as a function of suspension pH.

Prior to setting forth the invention, it may be helpful to provide an understanding of certain terms that will be used hereinafter:

Active Agents: As used herein "active agent" refers to drugs, pharmaceutical substances and bioactive agents. Active agents can be organic macromolecules including nucleic acids, synthetic organic compounds, polypeptides, peptides, proteins, polysaccharides and other sugars, and lipids. Peptides, proteins, and polypeptides are all chains of amino acids linked by peptide bonds. Peptides are generally considered to be less than 40 amino acid residues, but may include more. Proteins are polymers that typically contain more than 40 amino acid residues. The term polypeptide, as is known in the art and as used herein, can refer to a peptide, a protein, or any other chain of amino acids of any length containing multiple peptide bonds, though generally containing at least 10 amino acids. The active agents can fall under a variety of biological activity classes, such as vasoactive agents, neuroactive agents, hormones, anticoagulants, immunomodulating agents, cytotoxic agents, antibiotics, antiviral agents, antigens, and antibodies. More particularly, active agents may include, in a non-limiting manner, insulin and analogs thereof, growth hormone, parathyroid hormone (PTH), ghrelin, granulocyte macrophage colony stimulating factor (GM-CSF), glucagon-like peptide 1 (GLP-1), and analogs of such peptides, including ROSE-010, Texas Red, alkynes, cyclosporins, clopidogrel and PPACK (D-phenylalanyl-L-prolyl-L-arginine chloromethyl ketone), antibodies and fragments thereof, including, but not limited to, humanized or chimeric antibodies; F(ab), F(ab)$_2$, or single-chain antibody alone or fused to other polypeptides; therapeutic or diagnostic monoclonal antibodies to cancer antigens, cytokines, infectious agents, inflammatory mediators, hormones, and cell surface antigens. In some instances, the terms "drug" and "active agent" are used interchangeably.

Amino acid residue: An amino acid formed upon chemical digestion (hydrolysis) of a polypeptide at its peptide linkages. The amino acid residues described herein are preferably in the "L" isomeric form. However, the term "amino acid" encompasses every amino acid such as L-amino acid, D-amino acid, alpha-amino acid, beta-amino acid, gamma-amino acid, natural amino acid and synthetic amino acid or the like as long as the desired functional property is retained by the polypeptide. Further included are natural or synthetic amino acids which have been modified. $NH_2$ refers to the free amino group present at the amino terminus of a polypeptide. COOH refers to the free carboxy group present at the carboxy terminus of a polypeptide. Standard abbreviations for amino acid residues are used herein.

It should be noted that all amino acid residue sequences represented herein by formulae have a left-to-right orientation in the conventional direction of amino terminus to carboxy terminus. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Biliary dyskinesia refers to any motility abnormality in the biliary tree that causes pain and/or discomfort in the patient. This includes but is not restricted to gallbladder dysfunction, dysfunction of the biliary tract and dysfunction of the Sphincter of Oddi. Biliary dysfunction may be increased motility of an area of the biliary tract, decreased motility of an area of the biliary tract, or alternatively disordered control of motility, such as with spasms in the biliary tract.

Diketopiperazine: As used herein, "diketopiperazine" or "DKP" includes diketopiperazines and salts, derivatives, analogs and modifications thereof falling within the scope of the general Formula 1, wherein the ring atoms $E_1$ and $E_2$ at positions 1 and 4 are either O or N and at least one of the side-chains $R_1$ and $R_2$ located at positions 3 and 6 respectively contains a carboxylic acid (carboxylate) group. Compounds according to Formula 1 include, without limitation, diketopiperazines, diketomorpholines and diketodioxanes and their substitution analogs.

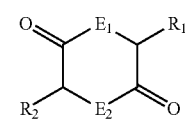

Formula 1

Diketopiperazines can be formed by cyclodimerization of amino acid ester derivatives, as described by Katchalski, et ah, (J. Amer. Chem. Soc. 68:879-80; 1946), by cyclization of dipeptide ester derivatives, or by thermal dehydration of amino acid derivatives in high-boiling solvents, as described by Kopple, et al., (J. Org. Chem. 33:862-64; 1968), the teachings of which are incorporated herein.

Methods for synthesis and preparation of diketopiperazines are well known to one of ordinary skill in the art and are disclosed in U.S. Pat. Nos. 5,352,461; 5,503,852; 6,071,497; 6,331,318; 6,428,771 and U.S. patent application Ser. No. 11/210,710. U.S. Pat. Nos. 6,444,226 and 6,652,885, describe preparing and providing microparticles of diketopiperazines in aqueous suspension to which a solution of active agent is added in order to bind the active agent to the particle. These patents further describe a method of removing a liquid medium by lyophilization to yield microparticles comprising an active agent, altering the solvent conditions of such suspension to promote binding of the active agent to the particle is taught in U.S. patent application Ser. No. 11/532,063 entitled "Method of Drug Formulation Based on Increasing the Affinity of Active Agents for Crystalline Microparticle Surfaces"; and Ser. No. 11/532,065 entitled "Method of Drug Formulation Based on Increasing the Affinity of Active Agents for Crystalline Microparticle Surfaces". See also U.S. Pat. No. 6,440,463 and U.S. patent application Ser. Nos. 11/210,709 and 11/208,087. In some instances, it is contemplated that the loaded diketopiperazine are dried by a method of spray drying as disclosed in, for example, U.S. patent application Ser. No. 11/678,046 and entitled "A Method For Improving the Pharmaceutic Properties of Microparticles Comprising Diketopiperazine and an Active Agent." Each of these patents and patent applications is incorporated by reference herein for all they contain regarding diketopiperazines.

Diketopiperazines, in addition to making aerodynamically suitable microparticles, can also facilitate the delivery of active agents by rapidly dissolving at physiologic pH thereby releasing the active agent and speeding its absorption into the circulation. Diketopiperazines can be formed into particles that incorporate a drug or particles onto which a drug can be adsorbed. The combination of a drug and a diketopiperazine can impart improved drug stability. These particles can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets or capsules.

In one embodiment, the diketopiperazine is 3,6-bis[4-(N-carboxy-2-propenyl)aminobutyl]-2,5-diketopiperazine or 3,6-di(fumaryl-4-aminobutyl)-2,5-diketopiperazine (fumaryl diketopiperazine, FDKP). The FDKP can comprise microparticles in its acid form or salt forms which can be aerosolized or administered in a suspension.

In another embodiment, the DKP is a derivative of 3,6-di(4-aminobutyl)-2,5-diketopiperazine, which can be formed by (thermal) condensation of the amino acid lysine. Exemplary derivatives include 3,6-di(succinyl-4-aminobutyl)-2,5-diketopiperazine, 3,6-di(maleyl-4-aminobutyl)-2,5-diketopiperazine, 3,6-di(glutaryl-4-aminobutyl)-2,5-diketopiperazine, 3,6-di(malonyl-4-aminobutyl)-2,5-diketopiperazine, 3,6-di(oxalyl-4-aminobutyl)-2,5-diketopiperazine, 3,6-di(fumaryl-4-aminobutyl)-2,5-diketopiperazine or 3,6-di(citraconyl-4-aminobutyl)-2,5-diketopiperazine and derivatives therefrom. The use of DKPs for drug delivery is known in the art (see for example U.S. Pat. Nos. 5,352,461, 5,503,852, 6,071,497, and 6,331,318, each of which is incorporated herein by reference for all that it teaches regarding diketopiperazines and diketopiperazine-mediated drug delivery). The use of DKP salts is described in co-pending U.S. patent application Ser. No. 11/210,710, which is hereby incorporated by reference for all it teaches regarding diketopiperazine salts. Pulmonary drug delivery using DKP microparticles is disclosed in U.S. Pat. No. 6,428,771, which is hereby incorporated by reference in its entirety. Further details related to adsorption of active agents onto crystalline DKP particles can be found in co-pending U.S. patent application Ser. Nos. 11/532,063 and 11/532,065 which are hereby incorporated by reference in their entirety. In the present disclosure, diketopiperazines are employed to facilitate the absorption of ROSE-010, thereby providing a stable formulation that is resistant to degradation.

Dissociation constant, Kd refers a measure to describe the strength of binding (or affinity or avidity) between receptors and their ligands, for example an antibody and its antigen. The smaller the Kd, the stronger the binding.

Drug delivery system: As used herein, "drug delivery system" refers to a system for delivering one or more active agents.

Dry powder: As used herein, "dry powder" refers to a fine particulate composition that is not suspended or dissolved in a propellant, carrier, or other liquid. It is not meant to necessarily imply a complete absence of all water molecules.

Early phase: As used herein, "early phase" refers to the rapid rise in blood insulin concentration induced in response to a meal. This early rise in insulin in response to a meal is sometimes referred to as first-phase. In more recent sources, first-phase is sometimes used to refer to the more rapid rise in blood insulin concentration of the kinetic profile achievable with a bolus IV injection of glucose in distinction to the meal-related response.

Effective amount: As used herein, an "effective amount" of a GLP-1/DKP dry powder formulation refers to that amount which will relieve to some extent one or more of the symptoms of the disease, condition or disorder being treated. In one embodiment, an "effective amount" of a VAL (8) GLP-1/DKP dry powder formulation would be in dosages of 10 µg to about 900 µg per administration, such as a dosage of from about 25 µg to about 500 µg per administration, or such as from about 50 µg to about 300 µg per administration.

Endocrine disease: The endocrine system is an information signal system that releases hormones from the glands to provide specific chemical messengers which regulate many and varied functions of an organism, e.g., mood, growth and development, tissue function, and metabolism, as well as sending messages and acting on them. Diseases of the endocrine system include, but are not limited to, diabetes mellitus, thyroid disease, and obesity. Endocrine disease is characterized by dysregulated hormone release (a productive pituitary adenoma), inappropriate response to signalling (hypothyroidism), lack or destruction of a gland (diabetes mellitus type 1, diminished erythropoiesis in chronic renal failure), reduced responsiveness to signaling (insulin resistance of diabetes mellitus type 2), or structural enlargement in a critical site such as the neck (toxic multinodular goiter). Hypofunction of endocrine glands can occur as result of loss of reserve, hyposecretion, agenesis, atrophy, or active destruction. Hyperfunction can occur as result of hypersecretion, loss of suppression, hyperplastic, or neoplastic change, or hyperstimulation. The term endocrine disorder encompasses metabolic disorders.

Excursion: As used herein, "excursion" can refer to blood glucose concentrations that fall either above or below a pre-meal baseline or other starting point. Excursions are generally expressed as the area under the curve (AUC) of a plot of blood glucose over time. AUC can be expressed in a variety of ways. In some instances there will be both a fall below and rise above baseline creating a positive and negative area. Some calculations will subtract the negative AUC from the positive, while others will add their absolute values. The positive and negative AUCs can also be considered separately. More sophisticated statistical evaluations can also be used. In some instances it can also refer to blood glucose concentrations that rise or fall outside a normal range. A normal blood glucose concentration is usually between 70 and 110 mg/dL from a fasting individual, less than 120 mg/dL two hours after eating a meal, and less than 180 mg/dL after eating. While excursion has been described here in terms of blood glucose, in other contexts the term may be similarly applied to other analytes.

Gallbladder dysfunction refers to any motility abnormality of the gall bladder including abnormal gallbladder emptying that causes biliary-type pain or discomfort.

Glucose elimination rate: As used herein, "glucose elimination rate" is the rate at which glucose disappears from the blood. It is commonly determined by the amount of glucose infusion required to maintain stable blood glucose, often around 120 mg/dL during the study period. This glucose elimination rate is equal to the glucose infusion rate, abbreviated as GIR.

Hyperglycemia: As used herein, "hyperglycemia" is a higher than normal fasting blood glucose concentration, usually 126 mg/dL or higher. In some studies hyperglycemic episodes were defined as blood glucose concentrations exceeding 280 mg/dL (15.6 mM).

Hypoglycemia: As used herein, "hypoglycemia" is a lower than normal blood glucose concentration, usually less than 63 mg/dL (3.5 mM). Clinically relevant hypoglycemia is defined as blood glucose concentration below 63 mg/dL or causing patient symptoms such as hypotonia, flush, and weakness that are recognized symptoms of hypoglycemia and that disappear with appropriate caloric intake. Severe hypoglycemia is defined as a hypoglycemic episode that required glucagon injections, glucose infusions, or help by another party.

Individual: As used here, the term "individual" or "subject" refer to a living animal. In preferred embodiments, the individual or subject is a mammal, including humans and non-human mammals such as dogs, cats, pigs, cows, sheep, goats, horses, rats, and mice. In the most preferred embodiment, the subject is a human.

In proximity: As used herein, "in proximity," as used in relation to a meal, refers to a period near in time to the beginning of a meal or snack.

Irritable Bowel Syndrome refers to a functional gastrointestinal disorder characterized most commonly by cramping, abdominal pain, discomfort, bloating, alteration of bowel habits, constipation, and/or diarrhea.

Microparticles: As used herein, the term "microparticles" includes particles of generally 0.5 to 100 microns in diameter and particularly those less than 10 microns in diameter. Various embodiments will entail more specific size ranges. The microparticles can be assemblages of crystalline plates with irregular surfaces and internal voids as is typical of those made by pH-controlled precipitation of the DKP acids. In such embodiments the active agents can be entrapped by the precipitation process or coated onto the crystalline surfaces of the microparticle. The microparticles can also be spherical shells or collapsed spherical shells comprised of DKP salts with the active agent dispersed throughout. Typically such particles can be obtained by spray drying a co-solution of the DKP and the active agent. The DKP salt in such particles can be amorphous. The forgoing descriptions should be understood as exemplary. Other forms of microparticles are contemplated and encompassed by the term.

Modified amino acid refers to an amino acid wherein an arbitrary group thereof is chemically modified. In particular, a modified amino acid chemically modified at the alpha-carbon atom in an alpha-amino acid is preferable.

Obesity refers to a condition in which excess body fat has accumulated to such an extent that health may be negatively affected. Obesity is typically assessed by BMI (body mass index) with BMI of greater than 30 kg/m$^2$.

Peripheral tissue: As used herein, "peripheral tissue" refers to any connective or interstitial tissue that is associated with an organ or vessel.

Periprandial: As used herein, "periprandial" refers to a period of time starting shortly before and ending shortly after the ingestion of a meal or snack.

Postprandial: As used herein, "postprandial" refers to a period of time after ingestion of a meal or snack. As used herein, late postprandial refers to a period of time 3, 4, or more hours after ingestion of a meal or snack.

Potentiation: Generally, potentiation refers to a condition or action that increases the effectiveness or activity of some agent over the level that the agent would otherwise attain. Similarly it may refer directly to the increased effect or activity. As used herein, "potentiation" particularly refers to the ability of elevated blood insulin concentrations to boost effectiveness of subsequent insulin levels to, for example, raise the glucose elimination rate.

Prandial: As used herein, "prandial" refers to a meal or a snack.

Preprandial: As used herein, "preprandial" refers to a period of time before ingestion of a meal or snack.

Prodrug: As used herein, the term "prodrug" means a substance that is transformed in vivo to yield a substance of the present disclosure. The transformation may occur by various mechanisms, such as through hydrolysis in blood. For example, when a compound contains a carboxylic acid functional group, a prodrug can comprise an ester formed by the replacement of the hydrogen atom of the acid group with a group including, but not limited to, groups such as for example $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N (alkoxycarbonyl)amino)ethyl having from 4 to 10 carbon atoms, 3-phthalidyl, 4 crotonolactonyl, gamma-butyrolacton-4-yl, di-N,N—$(C_1-C_2)$alkylamino$(C_2-C_3)$alkyl, carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Pulmonary inhalation: As used herein, "pulmonary inhalation" is used to refer to administration of pharmaceutical preparations by inhalation so that they reach the lungs and, in particular embodiments, the alveolar regions of the lung. Typically inhalation is through the mouth, but in alternative embodiments in can entail inhalation through the nose.

ROSE-010: As used herein, the term "ROSE-010" is used to refer to a GLP-1 analog with an Ala to Val amino acid substitution at position 8. ROSE-010 is also denoted Val (8) GLP-1 and/or Val$^8$ glucagon-like peptide-1 (7-37)OH.

Salt: As used herein, the term "salt" includes, but is not limited to, any possible base or acid addition salts of the diketopiperazine compounds disclosed herein. The acid addition salts are formed from basic compounds, whereas the base addition salts are formed from acidic compounds. All of these forms are within the scope of the present disclosure. A non-toxic pharmaceutically acceptable base addition salt of an acidic compound may be prepared by contacting the free acid form of the compound with a sufficient amount of a desired base to produce the salt in the conventional manner. The free acid form of the compound may be regenerated by contacting the salt form so formed with an acid, and isolating the free acid of the compound in the conventional manner. The free acid forms of the compounds differ from their respective salt forms in certain physical properties such as solubility, crystal structure, hygroscopicity, and the like, but otherwise the salts are equivalent to their respective free acid for purposes of delivering active agents according to the present disclosure.

Non limiting examples of counter ions for the base additions salts are a metal cation, such as an alkali or alkaline earth metal cation, or an amine, especially an organic amine. Examples of suitable metal cations include sodium cation (Na+), potassium cation (K+), magnesium cation (Mg2+), calcium cation (Ca2+), and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M. et al., "Pharmaceutical Salts," J. of Pharma. Sci., 1977; 66:1).

SO dysfunction is the term used to define motility abnormalities of the sphincter of Oddi (see Rome II: The functional Gastrointestinal Disorders $2^{nd}$ Edition)

Solvate: As used herein, the term "solvate" means a compound or a salt thereof that further includes a stoichiometric or non-stoichiometric amount of a solvent bound by non-covalent intermolecular forces. Preferred solvents are volatile, non-toxic, and/or acceptable for administration to humans in trace amounts. The solvated forms, including hydrated forms, are equivalent to unsolvated forms and are encompassed within the scope of the present invention.

TECHNOSPHERE®: As used herein, "TECHNOSPHERE®" refers to microparticles comprising a diketopiperazine, specifically 3,6-di(fumaryl-4-aminobutyl)-2,5-diketopiperazine (fumaryl diketopiperazine, FDKP).

DETAILED DESCRIPTION

There is disclosed a dry powder composition comprising glucagon-like peptide 1 (GLP-1) or a GLP-1 analog and a method for the treatment of a disease or a disorder which utilizes a drug delivery system that effectively delivers GLP-1 or a GLP-1 analog, including ROSE-010, to the pulmonary circulation so that the GLP-1 or analog thereof enters the pulmonary circulation and can be delivered in a therapeutically effective amounts to the site(s) of action. In one embodiment, the method of treatment of disease or disorder comprises administering to a patient in need of treatment a formulation which can deliver the active agent directly into the pulmonary circulation, and thereby to the arterial circulation, and can avoid degradation of the active agent such as peptides, which are degraded by enzymes or other mechanisms in the local peripheral and/or vasculature tissues of the lungs. In one aspect of this embodiment, the method comprises the effective therapeutic delivery of ROSE-010 using a drug delivery system which allows for very rapid lung absorption of the active agent into the arterial circulation and increases its effective bioavailability. In this embodiment, lower dosages of an active agent can be delivered by this method of administration. In similar embodiments effective doses can be achieved where they were not feasible by other modes of administration.

Indications

The inventors have identified the need to deliver drugs directly to the systemic circulation, in particular, the arterial circulation in a noninvasive fashion so that the drug reaches the target organ(s) prior to returning through the venous system. This approach may paradoxically result in a higher peak target organ exposure to active agents than would result from a comparable administration via an intravenous, subcutaneous or other parenteral route. A similar advantage can be obtained versus oral administration as, even with formulations providing protection from degradation in the digestive tract, upon absorption, the active agent will enter the venous circulation.

In embodiments herein, there is disclosed a pharmaceutical composition and a method for the treatment of disease, including but not limited to, Type II diabetes, obesity, cancer, ischemia, reperfused tissue injury, dyslipidemia, diabetic cardiomyopathy, myocardial infarction, acute coronary syndrome, catabolic changes after surgery, hyperglycemia, irritable bowel syndrome, stroke, neurodegenerative disorders, memory and learning disorders, islet cell transplant and regenerative therapy or any related diseases and/or conditions therefrom. Other diseases and/or conditions contemplated in the present invention are inclusive of any disease and/or condition related to those listed above that may be treated by administering a GLP-1/DKP, GLP-1 analog/DKP or ROSE-010/DKP dry powder formulation to a subject in need thereof. The dry powder formulation of the present invention may also be employed in the treatment of induction of beta cell differentiation in human cells of type-II diabetes and hyperglycemia.

In one embodiment, pharmaceutical composition and the method of treatment according to the invention may be used for any indication wherein GLP-1 is indicated, such as diabetes, ischemia, reperfused tissue injury, dyslipidemia, diabetic cardiomyopathy, myocardial infarction, acute coronary syndrome, obesity, catabolic changes after surgery, hyperglycemia, irritable bowel syndrome, stroke, neurodegenerative disorders, memory and learning disorders, islet cell transplant and regenerative therapy.

In yet another embodiment, a method of treatment of pain or discomfort and/or dyskinesia in the biliary tract (or "biliary dyskinesia") is provided. In this embodiment, the method comprises administering to a patient in need of treatment a therapeutically effective amount of GLP-1 or a GLP-1 analog, such as ROSE-010, wherein the formulation is administered by oral inhalation using, for example, a breath-powered inhaler. Other alternative routes of administration that may be employed in the present disclosure may include: bronchial administration by local aerosol delivery, injection, infusion, continuous infusion, localized perfusion bathing target cells directly, via a catheter, via a lavage, in creams, in lipid compositions (e.g., liposomes), or by other method, or any combination of the foregoing as would be known to one of ordinary skill in the art (see, for example, Remington's Pharmaceutical Sciences, 1990, incorporated herein by reference for all it contains regarding methods of administration).

In an exemplary embodiment, a method for treating diabetes and/or hyperglycemia comprises administering to a patient in need of treatment a dry powder composition or formulation comprising GLP-1 or a GLP-1 analog, such as ROSE-010, which can stimulate the rapid secretion of endogenous insulin from pancreatic β-cells without causing unwanted side effects such as profuse sweating, nausea, and vomiting. In one embodiment, the method of treating disease can be applied to a patient, including a mammal, suffering from Type 2 diabetes mellitus and/or hyperglycemia at dosages ranging from about 0.01 to about 3 mg of ROSE-010 in the formulation in a single dose. The method of treating hyperglycemia, diabetes, and/or obesity can be designed so that the patient can receive at least one dose of a ROSE-010 formulation in proximity to a meal or snack. In this embodiment, the dose of ROSE-010 can be selected depending on the patient's requirements. In one embodiment, pulmonary administration of ROSE-010 can comprise a ROSE-010 dose greater than 3 mg for example, in treating patients with type 2 diabetes.

In an exemplary embodiment, the method comprises the administration of the peptide hormone GLP-1 or a GLP-1 analog such as ROSE-010 to a patient for the treatment of hyperglycemia and/or diabetes, and obesity. The method comprises administering to a patient in need of treatment an effective amount of an inhalable composition or formulation comprising a dry powder formulation comprising GLP-1 or a GLP-1 analog such as ROSE-010 which can stimulate the rapid secretion of endogenous insulin from pancreatic β-cells without causing unwanted side effects, including, profuse sweating, nausea, and vomiting. In one embodiment, the method of treating disease can be applied to a patient, including a mammal, suffering with Type 2 diabetes mellitus and/or hyperglycemia at dosages ranging from about 0.01 mg to about 3 mg, or from about 0.2 mg to about 2 mg of GLP-1 in the dry powder formulation. In one embodiment, the patient or subject to be treated is a human. The GLP-1 can be administered immediately before a meal (preprandially), at mealtime (prandially), and/or at about 15, 30 or 45 minutes after a meal (postprandially). In one embodiment, a single dose of GLP-1 can be administered immediately before a meal and another dose can be administered after a meal. In a particular embodiment, about 0.5 mg to about 1.5 mg of GLP-1 can be administered immediately before a meal, followed by 0.5 mg to about 1.5 mg about 30 minutes after a meal. In this embodiment, the GLP-1 can be formulated with inhalation particles such as a diketopiperazine with or without pharmaceutical carriers and excipients. In one embodiment, pulmonary administration of the GLP-1 formulation can provide plasma concentrations of GLP-1 greater than 100 pmol/L without inducing unwanted adverse side effects, such as profuse sweating, nausea and vomiting to the patient.

In another embodiment, a method for treating a patient including a human with type 2 diabetes and hyperglycemia is provided, the method comprises administering to the patient an inhalable GLP-1 formulation comprising GLP-1 in a concentration of from about 0.5 mg to about 3 mg in FDKP microparticles wherein the levels of glucose in the blood of the patient are reduced to fasting plasma glucose concentrations of from 85 to 70 mg/dL within about 20 min after dosing without inducing nausea or vomiting in the patient. In one embodiment, pulmonary administration of GLP-1 at concentration greater than 0.5 mg in a formulation comprising fumaryl diketopiperazine (FDKP) microparticles lacks inhibition of gastric emptying.

In one embodiment, GLP-1 or an analog of GLP-1, including ROSE-010, can be administered either alone as the active ingredient in the composition, or with a dipeptidyl peptidase (DPP-IV) inhibitor such as sitagliptin or vildagliptin, or with one or more other active agents. DPP-IV is a ubiquitously expressed serine protease that exhibits postproline or alanine peptidase activity, thereby generating biologically inactive peptides via cleavage at the N-terminal region after X-proline or X-alanine, wherein X refers to any amino acid. Because both GLP-1 and GIP (glucose-dependent insulinotropic peptide) have an alanine residue at position 2, they are substrates for DPP-IV. DPP-IV inhibitors are orally administered drugs that improve glycemic control by preventing the rapid degradation of incretin hormones, thereby resulting in postprandial increases in levels of biologically active intact GLP-1 and GIP.

In this embodiment, the action of GLP-1 can be further prolonged, or augmented, in vivo, if required, using DPP-IV inhibitors. The combination of GLP-1, or an analog thereof and DPP-IV inhibitor therapy for the treatment of hyperglycemia and/or diabetes allows for reduction in the amount of active GLP-1 that may be needed to induce an appropriate insulin response from the β-cells in the patient. In another embodiment, the GLP-1 or ROSE-010 analog can be combined, for example, with other molecules other than a peptide, such as, for example, metformin. In one embodiment, the DPP-IV inhibitor or other molecules, including metformin, can be administered by inhalation in a dry powder formulation together with the GLP-1 or analog thereof in a co-formulation, or separately in its own dry powder formulation which can be administered concurrently with or prior to GLP-1 administration. In one embodiment, the DPP-IV inhibitor or other molecules, including metformin, can be administered by other routes of administration, including orally. In one embodiment, the DPP-IV inhibitor can be administered to the patient in doses ranging from about 1 mg to about 100 mg depending on the patient's need. Smaller concentrations of the DPP-IV inhibitor may be used when co-administered, or co-formulated with GLP-1. In this embodiment, the efficacy of GLP-1 therapy may be improved at reduced dosage ranges when compared to current dosage forms.

In embodiments described herein, GLP-1 can be administered at mealtime (in proximity in time to a meal or snack). In this embodiment, GLP-1 exposure can be limited to the postprandial period so it does not cause the long acting effects of current therapies. In embodiments wherein a DPP-IV inhibitor is co-administered, the DPP-IV inhibitor may be given to the patient prior to GLP-1 administration at mealtime. The amounts of DPP-IV inhibitor to be administered can range, for example, from about 0.10 mg to about 100 mg, depending on the route of administration selected. In further embodiments, one or more doses of the GLP-1 can be administered after the beginning of the meal instead of or in addition to a dose administered in proximity to the beginning of a meal or snack. For example one or more doses can be administered 15 to 120 minutes after the beginning of a meal, such as at 30, 45, 60, or 90 minutes.

In still yet a further embodiment, the method of treating hyperglycemia and/or diabetes comprises the administration of an inhalable dry powder composition comprising a diketopiperazine having the formula 2,5-diketo-3,6-di(4-X-aminobutyl)piperazine, wherein X is selected from the group consisting of succinyl, glutaryl, maleyl, and fumaryl. In this embodiment, the dry powder composition can comprise a diketopiperazine salt. In one embodiment, the diketopiperazine salt can be an inorganic salt including, sodium, potassium, magnesium, lithium, cesium, and calcium. In another embodiment, the diketopiperazine can be an organic salt, including, triethylamine, butylamine, diethanolamine and triethanolamine. In still yet another embodiment of the present invention, there is provided a dry powder composition, wherein the diketopiperazine is 2,5-diketo-3,6-di-(4-fumaryl-aminobutyl)piperazine or a salt thereof, with or without a pharmaceutically acceptable carrier, or excipient.

In certain embodiments, the method of treatment can comprise a dry powder formulation for inhalation comprising GLP-1, wherein the GLP-1 molecule is native GLP-1, or an amidated GLP-1 molecule, wherein the amidated GLP-1 molecule is GLP-1 (7-36) amide, or combinations thereof. In one embodiment, the GLP-1 can be an analog such as exenatide or ROSE-010.

In another embodiment, GLP-1 can be administered with insulin as a combination therapy and given prandially for the treatment of hyperglycemia and/or diabetes, for example, Type 2 diabetes mellitus. In this embodiment, the GLP-1 or analog thereof and insulin can be co-formulated in a dry powder formulation or administered separately to a patient in their own formulations. In one embodiment, wherein the GLP-1 and insulin are co-administered, both active ingredients can be co-formulated, for example, the GLP-1 and insulin can be prepared in a dry powder formulation for inhalation using diketopiperazine particles as described above. Alternatively, the GLP-1 and insulin can be formulated separately, wherein each formulation is for inhalation and comprises diketopiperazine particles. In one embodiment the GLP-1 and the insulin formulations can be admixed together in their individual powder form to the appropriate dosing prior to administration. In this embodiment, the insulin can be short-, intermediate-, or long-acting insulin and can be administered prandially.

In one embodiment for the treatment of Type 2 diabetes using co-administration of GLP-1 and insulin, an inhalable formulation comprising GLP-1 or an analog of GLP-1 can be administered to a patient prandially, simultaneously, or sequentially to an inhalable formulation of insulin such as insulin/FDKP. In this embodiment, in a Type 2 diabetic, GLP-1 can stimulate insulin secretion from the patient's pancreas, which can delay disease progression by preserving β-cell function (such as by promoting (β-cell growth) while prandially-administered insulin can be used as insulin replacement which mimics the body's normal response to a meal. In certain embodiments of the combination therapy, the insulin formulation can be administered by other routes of administration. In this embodiment, the combination therapy can be effective in reducing insulin requirements in a patient to maintain the euglycemic state. In one embodiment, the combination therapy can be applied to patients suffering with obesity and/or Type 2 diabetes who have had diabetes for less than 10 years and are not well controlled on diet and exercise or secretagogues. In one embodiment, the patient population for receiving GLP-1 and insulin combination therapy can be characterized by having β-cell function greater than about 25% of that of a normal healthy individual and/or, insulin resistance of less than about 8% and/or can have normal gastric emptying. In one embodiment, the inhalable GLP-1 and insulin combination therapy can comprise a rapid acting insulin such as insulin glulisine (APIDRA®), insulin lispro (HUMALOG®) or insulin aspart (NOVOLOG®), or a long acting insulin such as insulin detemir (LEVEMIR®) or insulin glargine (LANTUS®), which can be administered by an inhalation powder also comprising FDKP or by other routes of administration.

In another embodiment, a combination therapy for treating type 2 diabetes can comprise administering to a patient in need of treatment an effective amount of an inhalable insulin formulation comprising an insulin and a diketopiperazine, wherein the insulin can be a native insulin peptide, a recombinant insulin peptide, and further administering to the patient a long acting insulin analog which can be provided by inhalation in a formulation comprising a diketopiperazine or by another route of administration such as by subcutaneous injection. The method can further comprise the step of administering to the patient an effective amount of a DPP IV inhibitor. In one embodiment, the method can comprise administering to a patient in need of treatment, a formulation comprising a rapid acting or long acting insulin molecule and a diketopiperazine in combination with formulation comprising a long acting GLP-1, which can be administered separately and/or sequentially. GLP-1 therapy for treating diabetes in particular type 2 diabetes can be advantageous since administration of GLP-1 alone in a dry powder inhalable formulation or in combination with insulin or non-insulin therapies can reduce the risk of hypoglycemia.

In another embodiment, rapid acting GLP-1 and a diketopiperazine formulation can be administered in combination with a long acting GLP-1, such as exendin, for the treatment of diabetes, which can be both administered by pulmonary inhalation. In this embodiment, a diabetic patient suffering, for example, with Type 2 diabetes, can be administered prandially an effective amount of an inhalable formulation comprising GLP-1 so as to stimulate insulin secretion, while sequentially or sometime after such as from mealtime up to about 45 min, thereafter administering a dose of exendin-4. Administration of inhalable GLP-1 can prevent disease progression by preserving β-cell function while exendin-4 can be administered twice daily approximately 10 hours apart, which can provide basal levels of GLP-1 that can mimic the normal physiology of the incretin system in a patient. Both rapid acting GLP-1 and a long acting GLP-1 can be administered in separate, inhalable formulations. Alternatively, the long acting GLP-1 can be administered by other methods of administration including, for example, transdermally, intravenously or subcutaneously. In one embodiment, prandial administration of a short-acting and long acting GLP-1 combination may result in increased insulin secretion, greater glucagon suppression and a longer delay in gastric emptying compared to long acting GLP-1 administered alone. The amount of long acting GLP-1 administered can vary depending on the route of administration. For example, for pulmonary delivery, the long acting GLP-1 can be administered in doses from about 0.1 mg to about 1 mg per administration, immediately before a meal or at mealtime, depending on the form of GLP-1 administered to the patient.

In an embodiment, a kit for treating diabetes and/or hyperglycemia is provided which comprises a medicament cartridge for inhalation comprising a GLP-1 formulation and an inhalation device which is configured to adapt or securely engage the cartridge. In this embodiment, the kit can further comprise a DPP-IV inhibitor co-formulated with GLP-1, or in a separate formulation for inhalation or oral administration as described above. In variations of this embodiment, the kit does not include the inhalation device which can be provided separately.

In one embodiment, the pharmaceutical composition and the method for treatment can be utilized in a method for treating obesity so as to control or reduce food consumption in an animal such as a mammal. A therapeutically effective amount of an inhalable GLP-1 formulation can be administered to a patient in need of treatment, wherein an inhalable dry powder, GLP-1 formulation comprises GLP-1 and a diketopiperazine as described above. In this embodiment, the inhalable GLP-1 formulation can be administered alone or in combination with one or more endocrine hormone and/or anti-obesity active agents for the treatment of obesity. Exemplary endocrine hormones and/or anti-obesity active agents include, but are not limited to, peptide YY, oxyntomodulin, amylin, amylin analogs such as pramlintide acetate, and the like. In one embodiment, the anti-obesity agents can be administered in a co-formulation in a dry powder inhalable composition alone or in combination with GLP-1 together or in a separate inhalable dry powder composition for inhalation. Alternatively, in the combination of GLP-1 with one or more anti-obesity agents, or agents that can cause satiety, the GLP-1 formulation can be administered in a dry powder formulation and the anti-obesity agent can be administered by alternate routes of administration. In this embodiment, the method is targeted to reduce food consumption, inhibit food intake in the patient, decrease or suppress appetite, and/or control body weight. In this embodiment, a DPP-IV inhibitor can be administered to enhance or stabilize GLP-1 delivery into the pulmonary arterial circulation. In another embodiment, the DPP-IV inhibitor can be provided in combination with an insulin formulation comprising a diketopiperazine. In this embodiment, the DPP-IV inhibitor can be formulated in a diketopiperazine for inhalation or it can be administered in other formulation for other routes of administration such as by subcutaneous injection or oral administration.

In one embodiment, the present combination therapy using the drug delivery system can be applied to treat metabolic disorders or syndromes. In this embodiment, the drug delivery formulation can comprise a formulation comprising a diketopiperazine and an active agent, including GLP-1 and/or a long acting GLP-1 alone or in combination with one or more active agents such as a DPP-IV inhibitor and exendin, targeted to treat the metabolic syndrome. In this embodiment, at least one of the active agents to be provided to the subject in need of treatment and who may exhibit insulin resistance can be administered by pulmonary inhalation.

In another embodiment, the pulmonary administration of an inhalable dry powder formulation comprising GLP-1, or a GLP-1 analog and a diketopiperazine can be used as a diagnostic tool to diagnose the level or degree of progression of type 2 diabetes in a patient afflicted with diabetes in order to identify the particular treatment regime suitable for the patient to be treated. In this embodiment, a method for diagnosing the level of diabetes progression in a patient identified as having diabetes, the method comprising administering to the patient a predetermined amount of an inhalable dry powder formulation comprising GLP-1 and a diketopiperazine and measuring the endogenous insulin production or response. The administration of the inhalable dry powder formulation comprising GLP-1 can be repeated with predetermined amounts of GLP-1 until the appropriate levels of an insulin response is obtained for that patient to determine the required treatment regime required by the patient. In this embodiment, if a patient insulin response is inadequate, the patient may require alternative therapies. Patients who are sensitive or insulin-responsive can be treated with a GLP-1 formulation comprising a diketopiperazine as a therapy. In this manner, the specific amount of GLP-1 can be administered to a patient in order to achieve an appropriate insulin response to avoid hypoglycemia. In this and other embodiments, GLP-1 can induce a rapid release of endogenous insulin which mimics the normal physiology of insulin release.

In one embodiment, the pulmonary administration of an inhalable dry powder formulation comprising a GLP-1 or a GLP-1 analog, including ROSE-010, can be administered in therapeutically effective amounts to decrease pain and inhibit gastric motility in patients suffering with irritable bowel syndrome.

In one aspect of the disclosure, the method of treating functional dyspepsia and/or irritable bowel syndrome in a mammal in need of treatment, comprises administering to the mammal a therapeutically effective amount of a formulation by pulmonary inhalation, comprising a diketopiperazine having the formula: 3,6-bis[4-(N-carboxy-2-propenyl)amidobutyl]-2,5-diketopiperazine (fumaryl diketopiperazine, FDKP) and ROSE-010, a GLP-1 analog. In one embodiment, a method of administering an effective amount of a GLP-1 molecule or a GLP-1 analog to a subject in need of treatment of irritable bowel syndrome is provided, wherein the method comprises providing to said subject an inhalable dry powder formulation comprising a GLP-1 molecule or GLP-1 analog such as ROSE-010 and a diketopiperazine, wherein said administration is carried out by pulmonary delivery. In this and other embodiments related to the treatment of irritable bowel syndrome, the GLP-1 analog such as ROSE-010 is provided in a dry powder dosage form for inhalation and the dosage form comprises the GLP-1 analog in dosages of from about 0.01 mg to about 0.9 mg, from about 0.025 mg to about 0.5 mg, or from about 0.05 mg to about 0.3 mg is administered per administration. In one embodiment, the dry powder formulation can be provided, for example, using a single use inhaler.

In another embodiment, a method of forming a powder composition with an improved GLP-1 pharmacokinetic profile is provided, the method comprising the steps of: providing a GLP-1 analog such as Val (8) GLP-1, providing a particle-forming diketopiperazine in a solution, forming diketopiperazine particles, combining the Val (8) GLP-1 and the solution to form a co-solution, and removing solvent from the co-solution by spray-drying to form a powder for pulmonary inhalation with an improved GLP-1 pharmacokinetic profile.

GLP-1 Analogs

The present disclosure relates to the use of GLP-1 or a GLP-1 analog such as ROSE-010 in an inhalable dry powder formulation for the treatment of irritable bowel syndrome. The term "GLP-1 or GLP-1 analog" is used herein to refer to any molecule capable of binding to and activating the GLP-1 receptor. Methods for assaying the functional activity of the GLP-1 molecules for use in the present invention is described in the section entitled "Functional activity of GLP-1 molecule." The activity of the GLP-1 molecules for use in the present invention can be less potent or more potent than native GLP-1.

GLP-1 analogs are defined as molecules having one or more amino acid substitutions, deletions, inversions or additions, such as 15 or fewer, for example 13 or fewer, such as 11 or fewer, for example 9 or fewer, such as 7 or fewer for example 5 or fewer, such as 3 or fewer for example 2 or fewer. The amino acids may include D-amino acid forms. Numerous GLP-1 analogs are known in the art and are described in WO2007/028394 which is incorporated by reference. They include, but are not limited to, GLP-1 (7-34), GLP-1 (7-35), GLP-1 (7-36) NH2, Gln9-GLP-1 (7-37), d-Gln9-GLP1(7-37), Thr16-Lys18-GLP-1 (7-37), and Lys18-GLP-1 (7-37), Gly-GLP-1(7-36)NH$_2$, Gly'-GLP1(7-37)OH, Val'-GLP-1 (7-37)OH, Met8-GLP-1 (7-37)OH, acetyl-Lys9-GLP-1 (7-37), Thr9GLP-1 (7-37), D-Thr9-GLP-1 (7-37), Asn9-GLP-1 (7-37), D-Asn9-GLP-1 (7-37), Ser22-Arg23-Arg24-Gln26-GLP-1 (7-37), Arg23-GLP-1 (7-37), Arg24-GLP-1 (7-37), a-methyl-Ala8-GLP-1 (736)NH$_2$, and Gly'-Gln2'-GLP-1 (7-37) OH, and the like.

Other GLP-1 analogs consistent with the present invention are described by the formula: R$_3$-X-Glu-Gly-Thr-Phe-Thr-Ser-Asp-Val-Ser-Ser-Tyr-Leu-Y-Gly-Gln-Ala-Ala-Lys-Z-Phe-Ile-Ala-Trp-Leu-Val-Lys-Gly-Arg-R$_4$ (SEQ ID NO: 3) wherein: R$_3$ is selected from the group consisting of L-histidine, D-histidine, desaminohistidine, 2-amino-histidine, beta-hydroxy-histidine, homohistidine, alpha-fluoromethyl-histidine, and alpha-methyl-histidine; X is selected from the group consisting of Ala, Gly, Val, Thr, Ile, and alpha-methyl-Ala; Y is selected from the group consisting of Glu, Gln, Ala, Thr, Ser, and Gly; Z is selected from the group consisting of Glu, Gln, Ala, Thr, Ser, and Gly; and R$_4$ is selected from the group consisting of Gly-NH$_2$, and Gly-OH.

GLP-1 analogs also have been described in WO 91/11457, and include GLP-1(7-34), GLP-1 (7-35), GLP-1 (7-36), or GLP-1 (7-37), or the amide form thereof, and pharmaceutically-acceptable salts thereof, having at least one modification selected from the group consisting of:

(a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;
(b) substitution of an oxidation-resistant amino acid for tryptophan at position 31;
(c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26;
(d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and
(e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions described in (a), (b), (d), and (e), the substituted amino acids can optionally be in the D-form and the amino acids substituted at position 7 can optionally be in the N-acylated or N-alkylated form.

Preferred GLP-1 molecules used in the present inventive formulation also include analogs of GLP-1 (7-37)NH$_2$ and GLP-1 (7-37) in which one or more amino acids which are not present in the original sequence are added or deleted, and derivatives thereof.

Specifically, His and desamino-histidine are preferred for R$_3$ and/or Ala, Gly and Val are preferred at the "X" position. Also, Glu and Gln are preferred for at the "Y" position. Glu and Gln are preferred at the "Z" position and Gly-OH is preferred for R$_4$.

A particularly preferred GLP-1 analog is known as Val (8) GLP-1 (ROSE-010: SEQ ID NO: 1).

Functional Activity of GLP-1 Molecule

The GLP-1 molecules described herein are capable of binding to and activating the GLP-1 receptor.

The receptor activity can be measured using different techniques such as detecting a change in the intracellular conformation of the receptor, in the G-protein coupled activities and/or in the intracellular messengers.

Different techniques for measuring the receptor activity are described in WO2007/028394 which is incorporated by reference herein.

Formulation

A method of introducing an active agent into the circulatory system of a mammal is disclosed herein. The method comprises a drug delivery system which prevents deactivation or degradation of the active agent being administered to a patient in need of treatment. In particular, the drug delivery system is designed for pulmonary drug delivery such as by inhalation, for delivery of active agents to the pulmonary circulation in a therapeutically effective manner. The drug delivery system has advantages over other methods of drug delivery, for example, oral, subcutaneous and intravenous administration of drug products such as proteins and peptides that are sensitive to enzymatic deactivation or degradation in the local peripheral and vascular tissue before reaching the target site.

In one embodiment disclosed herein, a method for providing an active agent to a patient in need thereof is disclosed comprising selecting an active agent subject to degradation in the patient wherein effectiveness of the active agent is reduced by the degradation, associating the active agent with a diketopiperazine to produce a pharmaceutical composition suitable for pulmonary inhalation, and providing the pharmaceutical composition to the patient.

In another embodiment, the degradation occurs in venous blood circulation, in a peripheral tissue, in the gastrointestinal system, or in the liver.

Also disclosed herein is a method of treating disease comprising selecting a patient being treated with or a patient with a condition treatable by a labile active agent, providing a composition comprising the labile active agent in association with a diketopiperazine, and administering the composition to the patient via pulmonary inhalation, thereby treating the disease or condition.

In another embodiment, the pharmaceutical composition is an inhalable dry powder formulation. In yet another embodiment, the inhalable dry powder formulation further comprises a pharmaceutically acceptable carrier or excipient.

In one embodiment, the inhalable dry powder formulation is provided to the patient by pulmonary inhalation using a dry powder inhalation system.

In yet another embodiment, the active agent is a protein, a peptide, or an analog thereof. In another embodiment, the active agent is an endocrine hormone or an analog thereof. The endocrine hormone is a hormone associated with diabetes, hyperglycemia and/or obesity. In another embodiment, the diabetes is type 2 diabetes mellitus.

In another embodiment of the disclosed method, the step of administering the composition to the patient comprises pulmonary administration of the composition using a dry powder inhaler comprising a cartridge, such as a unit dosing cartridge.

The methods of delivery presented in various embodiments herein can provide a more direct path to an active agent's site of action. Thus in addition to the avoidance of degradation, though in some instances still in part due to it, the biodistribution of the active agent delivered by inhalation can differ from that achieved with modes of delivery that entail absorption into, and travel through, the venous circulation prior to reaching sites of action in the body. For active agents such as GLP-1 and analogs thereof, with multiple effects and sites of action, a different constellation of effects may be observed when administered via inhalation as the relative concentrations at different sites of action will differ from that achieved using other modes of administration. This can further contribute to greater effective bioavailability, avoidance of unwanted effects, and the like.

In one embodiment, the dry powder formulation for use with the methods disclosed herein comprises particles comprising a GLP-1 analog molecule, preferably ROSE-010, and a diketopiperazine or a pharmaceutically acceptable salt thereof.

In one embodiment, the inhalable formulation comprises a dry powder formulation comprising the above-mentioned active ingredient with a diketopiperazine, including 2,5-diketo-3,6-di(4-X-aminobutyl)piperazine, wherein X is selected from the group consisting of succinyl, glutaryl, maleyl, and fumaryl, or a salt of the diketopiperazine. In this embodiment, the inhalable formulation can comprise microparticles for inhalation comprising the active ingredient with the aerodynamic characteristics as described above. In one embodiment, the amount of active ingredient can be determined by one of ordinary skill in the art, however, the present microparticles can be loaded with various amounts of active ingredient as needed by the patient. For example, for oxyntomodulin, the microparticles can comprise from about 1% (w/w) to about 75% (w/w) of the active ingredient in the formulation. In certain embodiments, the inhalable formulations can comprise from about 10% (w/w) to about 30% (w/w) of the pharmaceutical composition and can also comprise a pharmaceutically acceptable carrier, or excipient, such as a surfactant, such as polysorbate 80. In this embodiment, oxyntomodulin can be administered to the patient from once to about four times a day or as needed by the patient with doses ranging from about 0.05 mg up to about 5 mg in the formulation. In particular embodiments, the dosage to be administered to a subject can range from about 0.1 mg to about 3.0 mg of oxyntomodulin. In one embodiment, the inhalable formulation can comprise from about 50 pmol to about 700 pmol of oxyntomodulin in the formulation.

In one embodiment, the formulation comprising the active ingredient can be administered to the patient in a dry powder formulation by inhalation using a dry powder inhaler such as the inhaler disclosed, for example, in U.S. Pat. No. 7,305,986 and U.S. patent application Ser. No. 10/655,153 (US 2004/0182387), which disclosures are incorporated herein by reference. Repeat inhalation of dry powder formulation comprising the active ingredient can also be administered between meals and daily as needed. In some embodiments, the formulation can be administered once, twice, three or four times a day.

In this embodiment, the carrier can be associated with one or more active agents to form a drug/carrier complex which can be administered as a composition that avoids rapid degradation of the active agent in the peripheral and vascular venous tissue of the lung. In one embodiment, the carrier is a diketopiperazine.

The method described herein utilizes a drug delivery system that effectively delivers a therapeutic amount of an active agent, including peptide hormones, rapidly into the arterial circulation. In one embodiment, the active agent include, but are not limited to peptides such as ROSE-010 and other GLP-1 analogs, which are sensitive to degradation or deactivation, formulating the active agent into a dry powder composition comprising a diketopiperazine, and delivering the active agent(s) into the systemic circulation by pulmonary inhalation using a cartridge and a dry powder inhaler. In one embodiment, the method comprises selecting a peptide that is sensitive to enzymes in the local vascular or peripheral tissue of, for example, the dermis, or lungs. The present method allows the active agent to avoid or reduce contact with peripheral tissue, venous or liver metabolism/degradation. In another embodiment, for systemic delivery of the active agent should not have specific receptors in the lungs.

The ROSE-010 formulation is administered by inhalation such as by pulmonary administration. In this embodiment, pulmonary administration can be accomplished by providing ROSE-010 in a dry powder formulation for inhalation. The dry powder formulation is a stable composition and can comprise microparticles which are suitable for inhalation and which dissolve rapidly in the lung and rapidly deliver ROSE-010 to the pulmonary circulation. Depending on the particle size, the ROSE-010 pharmaceutical composition can be delivered by inhalation to specific areas of the respiratory system. Suitable particle sizes for pulmonary administration can be less than 10 μm in diameter, and preferably less than 5 μm. Exemplary particle sizes that can reach the pulmonary alveoli range from about 0.5 μm to about 5.8 μm in diameter. Such sizes refer particularly to aerodynamic diameter, but often also correspond to actually physical diameter as well. Such particles can reach the pulmonary capillaries, and can avoid extensive contact with the peripheral tissue in the lung. In this embodiment, the drug can be delivered to the arterial circulation in a rapid manner and avoid degradation of the active ingredient by enzymes or other mechanisms prior to reaching its target or site of action in the body. In one embodiment, dry powder compositions for pulmonary inhalation comprising ROSE-010 and DKP can comprise microparticles wherein from about 35% to about 75% of the microparticles have an aerodynamic diameter of less than 5.8 μm. Additionally the ROSE-010/DKP particles can be made small enough for incorporation into a intravenous suspension dosage form. For oral delivery, the particles can be incorporated into a suspension, tablets or capsules.

Dosage

In one aspect, the GLP-1 analog is resistant to degradation and can have a longer life than native GLP-1 in the circulation. In this and other embodiments, the GLP-1 analog is administered in dosages ranging from about 0.01 mg to about 3 mg in the formulation and the dosing regimen can be daily, or more than once a day. In administering a ROSE-010/DKP composition of the present invention to a subject in need thereof, the actual dosage amount of the composition can be determined on the basis of physical and physiological factors such as body weight, severity of condition, the type of disease being treated, previous or concurrent therapeutic interventions, idiopathy of the patient and the route of administration. A skilled artisan would be able to determine actual dosages based on one or more of these factors.

The ROSE-010/DKP formulation can be administered once or more than once, depending the disease or condition to be treated. In particular in relation to treatment of diabetes the formulation may be administered several times per day, such as before the meals. In relation to treatment of irritable bowel syndrome, the formulation may be administered when there is a need for treating pain spasms.

In one embodiment, the method of treatment comprises administering ROSE-010 in therapeutically effective amounts that can produce a bioavailability of greater than 50 pMol/L, or greater than 100 pMol/L by pulmonary inhalation. In one embodiment, the DKP-ROSE-010 formulation delivered by pulmonary inhalation can produce plasma concentration of the ROSE-010 analog greater than 500 pMol/L. In this embodiment, the GLP-1 analog has the amino acid sequence: His-Val-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-OH(ROSE-010; SEQ ID NO: 1). In this and other embodiments, the formulation comprising ROSE-010 can decrease pain and inhibit gastric motility in patients suffering with irritable bowel syndrome.

In one embodiment, a patient is administered an inhalable GLP-1 formulation in a dosing range wherein the amount of GLP-1 is from about 0.01 mg to about 3 mg, or from about 0.02 mg to about 2.5 mg, or from about 0.2 mg to about 2 mg of the formulation. In one embodiment, a patient with type 2 diabetes can be given a GLP-1 dose greater than 3 mg. In this embodiment, the GLP-1 can be formulated with inhalation particles such as a diketopiperazines with or without pharmaceutical carriers and excipients. In one embodiment, pulmonary administration of the GLP-1 formulation can provide plasma concentrations of GLP-1 greater than 100 pmol/L without inducing unwanted adverse side effects, such as profuse sweating, nausea and vomiting to the patient.

EXAMPLES

The following examples are included to demonstrate certain embodiments of the methods and compositions disclosed herein. It should be appreciated by those of skill in the art that the techniques disclosed in the examples elucidate representative techniques that function well in the practice of the methods disclosed herein. However, those of skill in the art should, in light of the present disclosure, appreciate that many changes can be made in the specific embodiments that are disclosed and still obtain a like or similar result without departing from the spirit and scope of the disclosure.

Example 1

Preparation of Diketopiperazine Formulation Comprising a GLP-1 Analog, ROSE-010

Protein Adsorption onto TECHNOSPHERE® Particles

Diketopiperazine particles were prepared using procedures as disclosed in U.S. patent application Ser. No. 11/735,957, which disclosure is incorporated by reference as it pertains herein.

Effect of pH: A solution of ROSE-010 (5 mg/mL) in 7% acetic acid was mixed with a TECHNOSPHERE® particle suspension. Quantities were selected to provide a final dry powder containing 10% ROSE-010 by weight. The pH of the resulting suspension was adjusted to ensure complete adsorption of ROSE-010 onto the TECHNOSPHERE® particles (FIG. 1). Essentially all of the peptide was adsorbed at pH 4.5.

Constant pH

In a second adsorption experiment, a solution of ROSE-010 (5 mg/mL) was prepared at pH 3.0 and added to a TECHNOSPHERE® particle suspension at pH 3.0. Quantities were selected to provide a final dry powder containing 10% ROSE-010 by weight. The mixed suspension was maintained at pH 3.0 to reduce potential aggregation of the ROSE-010 peptide. Under these conditions, only 2.4% of the ROSE-010 was adsorbed to the TECHNOSPHERE® particles.

Preparation of Prototype ROSE-010 TECHNOSPHERE® Powders

Powder Preparation: Fumaryl diketopiperazine-ROSE-010 particles in suspension were suspended in water. Water was removed from the final suspensions from each adsorption experiment by lyophilization to give 200-300 mg of each powder.

Determination of ROSE-010 Content in Prototype Powders by HPLC

HPLC Method Development

Figure 2:
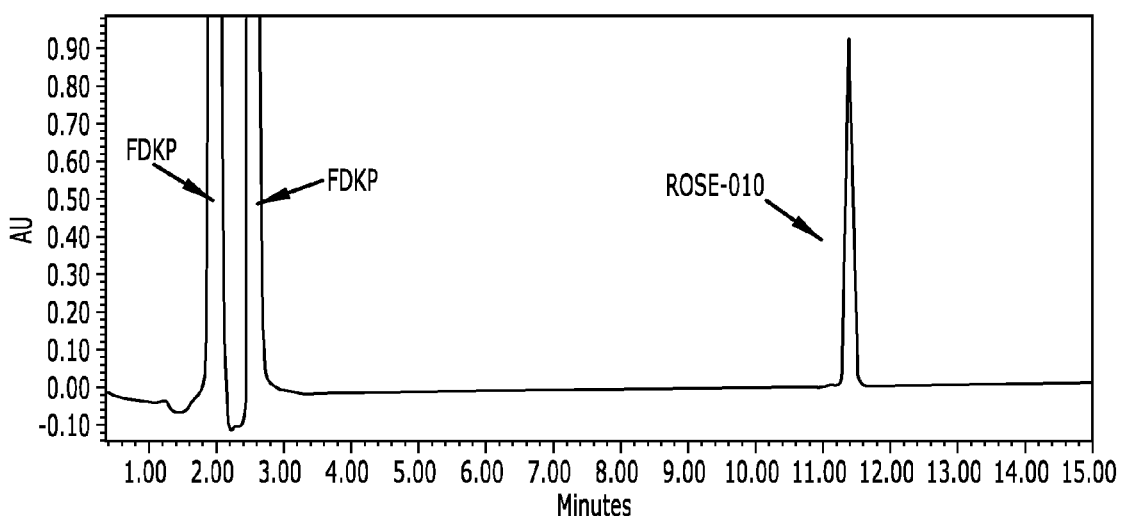
FIG. 2 depicts a representative high pressure liquid chromatograph (HPLC) chromatogram of an FDKP-GLP-1 analog profile in an initial assay for powder adsorption studies of the powder.
Figure 3:
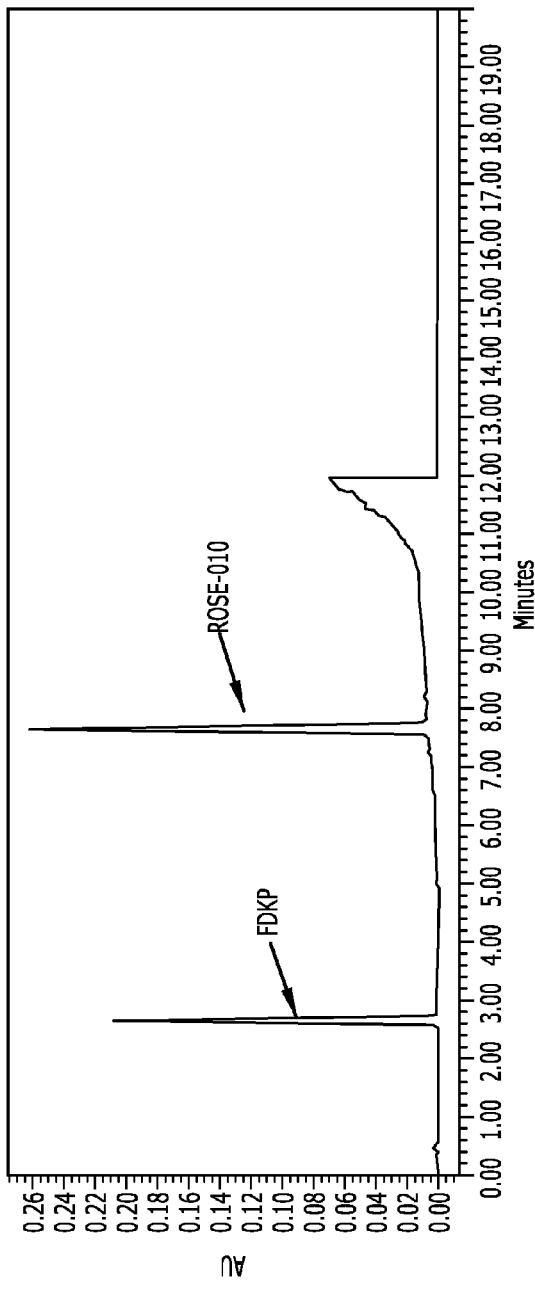
FIG. 3 depicts a representative HPLC chromatogram of an FDKP-GLP-1 analog in a refined assay for powder and test article analysis of the powder.
Figure 4:
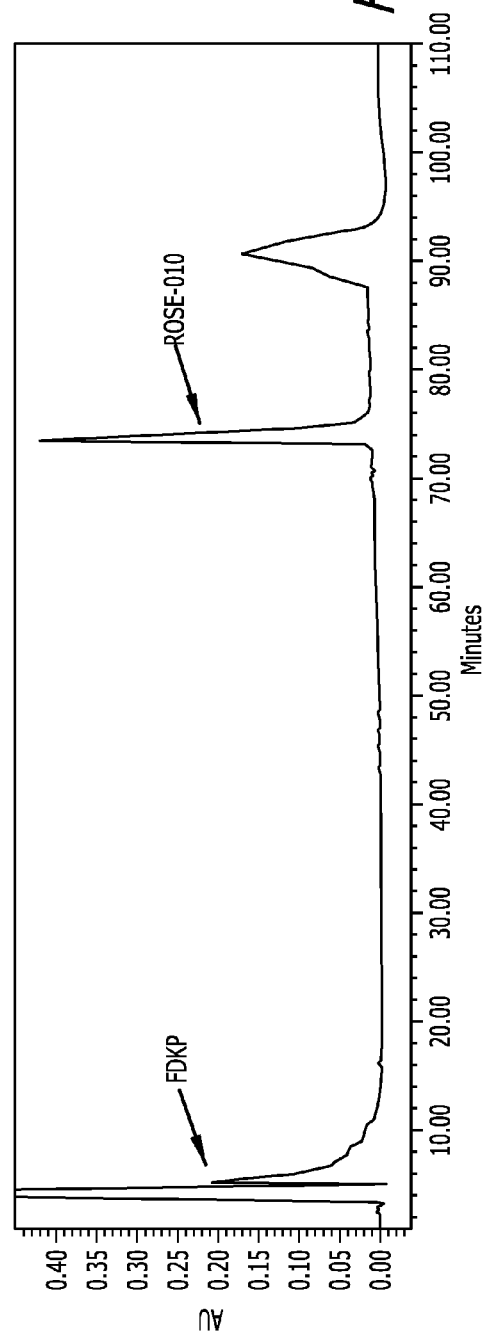
FIG. 4 depicts a representative HPLC chromatogram of an FDKP-GLP-1 analog in a related assay of the powder.
Figure 5:
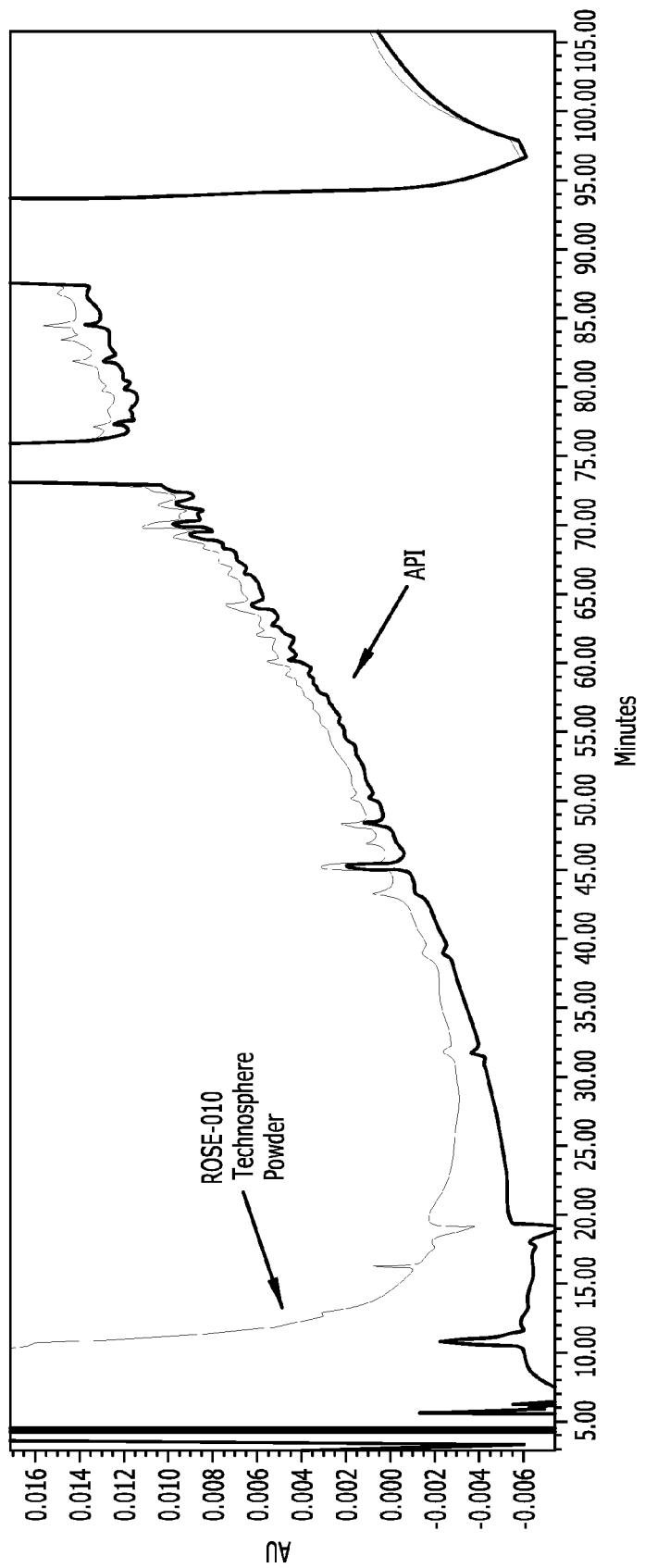
FIG. 5 depicts a representative HPLC chromatogram of the GLP-1 analog ROSE-010 alone and FDKP-ROSE-010.

Several HPLC methods previously developed by MannKind Corporation (Valencia, Calif.) for quantifying peptides in the presence of FDKP (primary component of TECHNOSPHERE® powders) were used to evaluate ROSE-010 TECHNOSPHERE® powders. The first method was a rapid assessment method to quantify ROSE-010 in the initial prototype powders. This method showed no interference between FDKP and ROSE-010 (FIG. 2). A more refined assay method was used to quantitative ROSE-010 in test articles, dosing solutions, and stability samples (FIG. 3). A third method was evaluated to monitor related substances in stability samples (FIG. 4). Comparing chromatograms of ROSE-010 alone and ROSE-010 in the TECHNOSPHERE® powder (FIG. 5) using the related substances method showed no significant increase in related compounds due to the formulation process. All of these methods are suitable for analyzing ROSE-010 TECHNOSPHERE® powders during these studies.

The ROSE-010 TECHNOSPHERE® powders were analyzed by HPLC. The target and measured ROSE-010 content for the prototype powders are comparable (Table 1). This formulation process facilitates quantitative recovery of the peptide.

TABLE 1

Percent ROSE-010 in prototype powders.

| Powder | Target ROSE-010 content (%) | Assayed ROSE-010 content (%) |
|---|---|---|
| Powder prepared at pH 4.5 | 10.0 | 10.1 |
| Powder prepared at pH 3.0 | 10.0 | 9.2 |

Aerodynamic Characterization by Cascade Impaction

Figure 6:
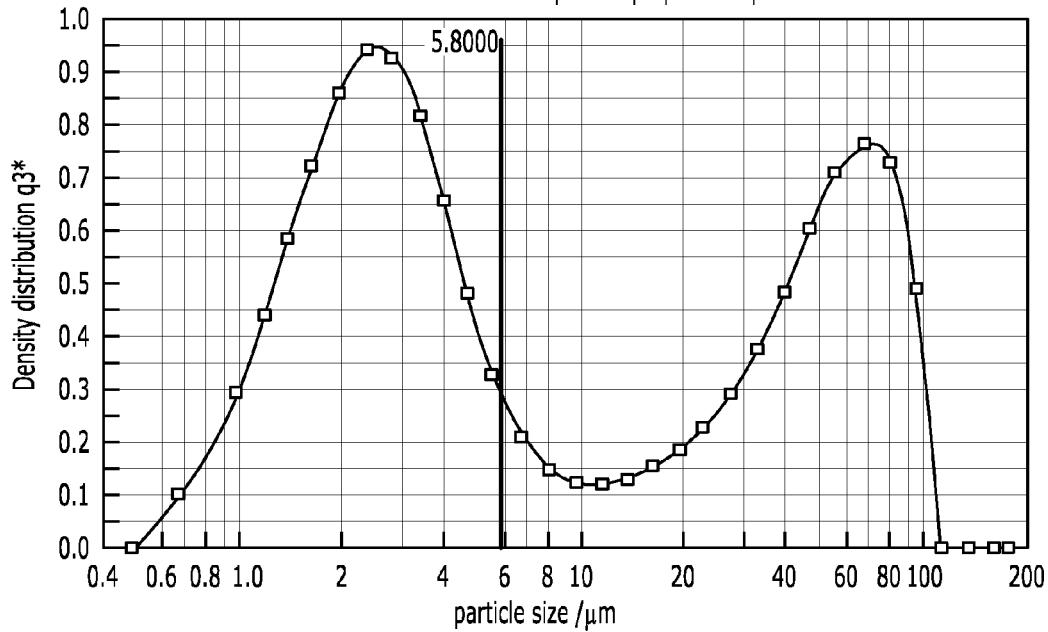
FIG. 6 depicts the particle size distribution for a powder sample of FDKP-ROSE-010 prepared at pH 4.5 using a SYMPATEC™ RODOS procedure.
Figure 7:
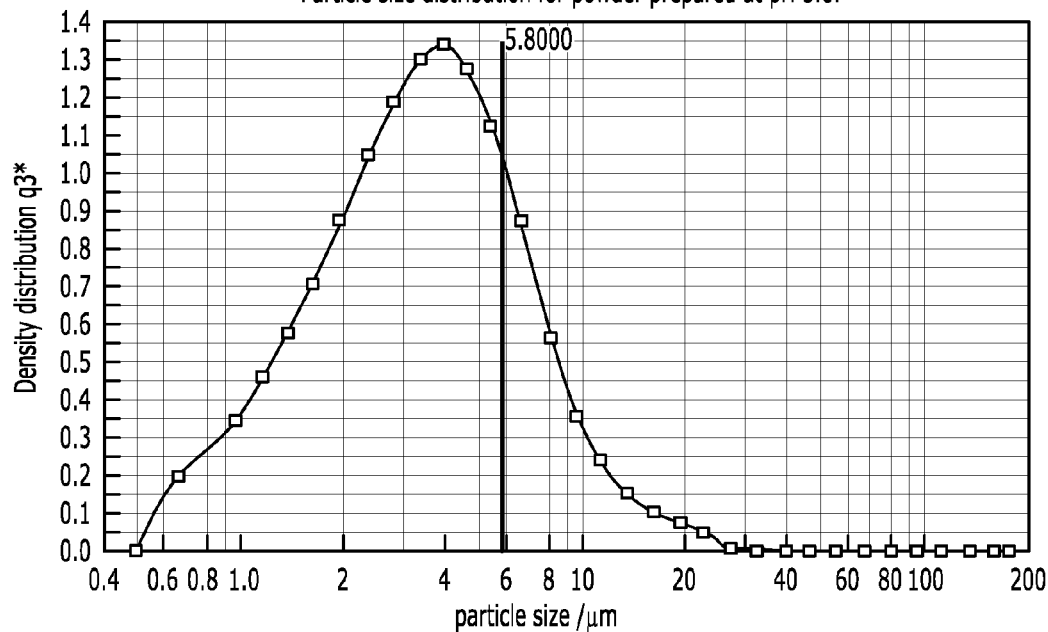
FIG. 7 depicts a representative SYMPATEC™ RODOS profile of the particle size distribution of the FDKP and ROSE-010 powder formulation prepared at pH 3.0.

The prototype ROSE-010 TECHNOSPHERE® powders were filled into inhaler cartridges (5 mg into each of 5 cartridges) and analyzed by discharge through MannKind Corporation's next generation inhaler into an Andersen cascade impactor. Aerodynamic performance was measured as respirable fraction of fill contents (% RF/fill) and cartridge emptying. The particle size distribution of the powders was also analyzed by laser diffraction analysis using a SYMPATEC™ RODOS system and the results are shown in FIGS. 6 and 7, and Table 2. The data show the performance of the powder prepared at pH 3.0 was better than the performance of the powder prepared by pH adjustment (Table 2). Cartridge emptying was >98% for both powders. FIGS. 6 and 7, and Table 2 show that of the powder that emptied from the cartridge, 34% of the powder prepared at pH 4.5 was in the respirable range and 47% of the powder prepared at pH 3.0 was in the respirable range.

TABLE 2

Aerodynamic data for prototype powders.

| | Cascade impactor | | SYMPATEC ™ RODOS | |
|---|---|---|---|---|
| Powder | % RF/fill | % Cartridge Emptying | Median diameter (μm) | % < 5.8 μm by RODOS |
| Powder prepared at pH 4.5 | 34 | 100 | 4.35 | 55 |
| Powder prepared at pH 3.0 | 47 | 98 | 3.42 | 79 |

The RODOS results show that powder prepared at pH 4.5 has a bimodal particle size distribution as illustrated by the scan shown at FIG. 6. One particle size population was centered on 2.5 μm and the other at 60-70 μm (FIG. 6). Only about 55% of the particles were in the respirable range (<5.8 µm). The powder prepared at pH 3.0 (FIG. 7) exhibits a single mode at about 4 µm and more of the particles are sized in the respirable range (below 5.8 µm).

Example 2

Pulmonary Insufflation of ROSE-010 (GLP-1 Peptide Analog) Completely Suppresses the Migrating Myoelectric/Motor Complex in the Conscious Rat: Comparison with the Intravenous and Subcutaneous Administrations The aim of these studies were to compare ROSE-010 in the MMC model pulmonary insufflation of ROSE-010 TECHNOSPHERE® powder compared to ROSE-010 administered by subcutaneous (SC) or intravenous (IV) injection. Studies were carried out in 10 rats with a jugular vein catheter and bipolar electrodes implanted at 5, 15, and 25 cm distal to the pylorus. Myoelectric activity was continuously recorded over 6-8 hours. After a control period of four MMC cycles, animals were briefly (4 min) anesthetized with Isoflurane 3-4% and rapidly insufflated with air or ROSE-010 TECHNOSPHERE® powder at doses of 0.2 and 0.1 mg/kg ROSE-010. Alternatively, ROSE-010 was administered by IV or SC injection at 0.1 mg/kg. Recording was continued until four MMC cycles were resumed.

Formulations for Pharmacodynamic (PD) Studies

Figure 8:
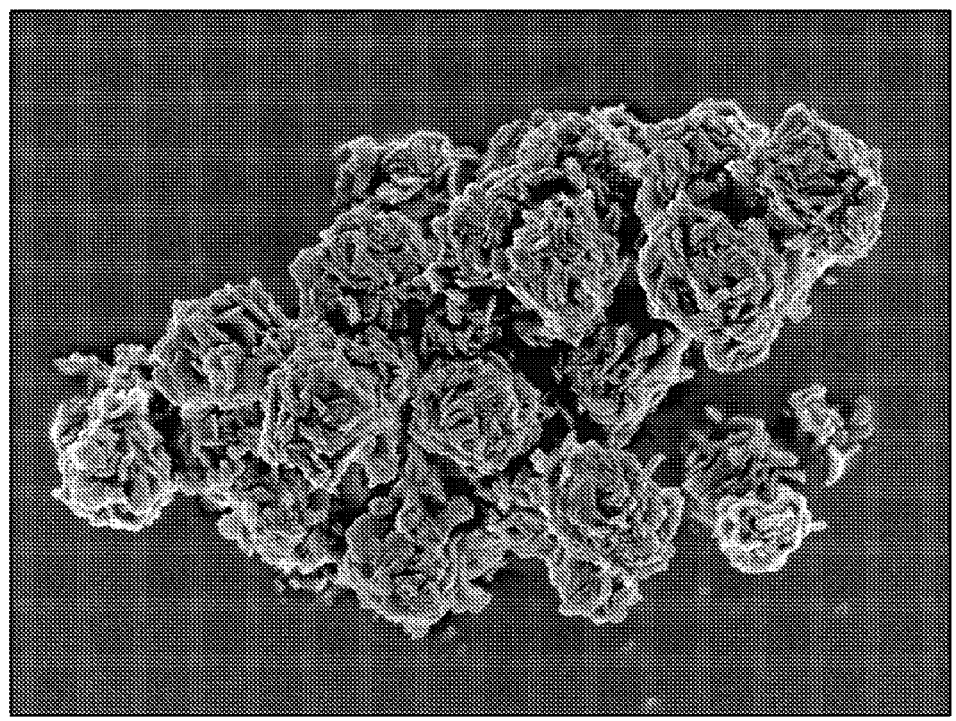
FIG. 8 depicts a representative scanning electron micrograph of the powder particles comprising the GLP-1 analog ROSE-010, and FDKP, the powder which was used in the further pharmacodynamic studies.

Based on the rat pharmacokinetic study, the pH 4.5 formulation process was selected to prepare powder for a subsequent pharmacodynamic study. This powder was characterized (Table 3). An SEM micrograph (FIG. 8) shows the agglomerates previously observed for ROSE-010 TECHNOSPHERE® powder prepared at pH 4.5. The scanning electronmicrograph of the sample powder showing the particle composition of the powder is shown in FIG. 8. The particles appear somewhat spherical with numerous plate-like structures

TABLE 3

Analytical results for the pharmacodynamic 10% ROSE-010 TECHNOSPHERE ® powder.

| Target ROSE-010 content (%) | % ROSE-010 | % RF/Fill | % Cartridge Emptying |
|---|---|---|---|
| 10.0 | 9.1 | 24 | 98 |

Stability: The ROSE-010 TECHNOSPHERE® powder used for the PD study was placed on a three month open dish stability evaluation at −20° C. and at 25° C./60% relative humidity (RH). Sampling time points were selected at 2 weeks, 1 month, 2 months and 3 months after initiation of the studies. The ROSE-010 stability was unchanged after one month at freezer conditions (Table 4). At 25° C./60% RH, the ROSE-010 stability decreased slightly over a period of three months (Table 5). A review of ROSE-010 assay calculations identified an error for the value at release ($t_0$).

TABLE 4

Stability data (−20° C.) for 10% ROSE-010 TECHNOSPHERE ® powder.

| | release ($t_0$) | | 2 weeks | | 1 month | | 2 months | | 3 months | |
|---|---|---|---|---|---|---|---|---|---|---|
| | Appearance | | | | | | | | | |
| | White powder | | White powder | | White powder | | White powder | | White powder | |
| | Wt % ROSE-010 (Relative to $t_0$) | | | | | | | | | |
| | 8.6 (100%) | | 9.0 (104%) | | 9.1 (106%) | | 9.2 (107%) | | 9.1 (105%) | |
| | RRT | % | RRT | % | RRT | % | RRT | % | RRT | % |
| Related Substances | 0.59 | 0.21 | 0.63 | 0.20 | 0.64 | 0.29 | 0.63 | 0.18 | 0.59 | 0.19 |
| | 0.62 | 0.30 | 0.65 | 0.33 | 0.94 | 0.21 | 0.66 | 0.26 | 0.62 | 0.31 |
| | 0.87 | 0.18 | 0.95 | 0.25 | 0.95 | 0.23 | 0.85 | 0.15 | 0.83 | 0.18 |
| | 0.94 | 0.23 | 0.96 | 0.30 | 1.03 | 1.72 | 0.89 | 0.19 | 0.87 | 0.17 |
| | 0.95 | 0.30 | 1.03 | 1.07 | 1.05 | 0.25 | 0.95 | 0.22 | 0.94 | 0.23 |
| | 1.03 | 1.48 | 1.05 | 0.16 | 1.13 | 0.16 | 0.96 | 0.22 | 0.95 | 0.28 |
| | 1.05 | 0.16 | 1.10 | 0.17 | 1.15 | 0.23 | 1.03 | 1.28 | 0.97 | 0.16 |
| | 1.11 | 0.17 | 1.13 | 0.23 | 1.26 | 0.21 | 1.05 | 0.17 | 1.03 | 1.24 |
| | 1.14 | 0.15 | | | | | 1.13 | 0.16 | 1.15 | 0.17 |
| | 1.15 | 0.24 | | | | | 1.14 | 0.31 | 1.17 | 0.25 |
| | | | | | | | 1.26 | 0.21 | 1.30 | 0.29 |

TABLE 5

Stability data (25° C./60% RH) for 10% ROSE-010 TECHNOSPHERE ® powder.

Storage Condition: 25° C./60% RH
Parameter (Unit)

| | release ($t_0$) | 2 weeks | 1 month | 2 months | 3 months |
|---|---|---|---|---|---|
| Appearance | White powder | White powder | White powder | White powder | White powder |
| Wt % ROSE-010 (Relative to $t_0$) | 8.6 (100%) | 8.5 (99%) | 8.4 (98%) | 8.3 (97%) | 8.2 (95%) |

| | RRT | % | RRT | % | RRT | % | RRT | % | RRT | % |
|---|---|---|---|---|---|---|---|---|---|---|
| Related Substances | 0.59 | 0.21 | 0.63 | 0.22 | 0.60 | 0.22 | 0.63 | 0.27 | 0.59 | 0.31 |
| | 0.62 | 0.30 | 0.66 | 0.34 | 0.63 | 0.31 | 0.66 | 0.28 | 0.61 | 0.37 |
| | 0.87 | 0.18 | 0.69 | 0.15 | 0.88 | 0.17 | 0.85 | 0.15 | 0.65 | 0.17 |
| | 0.94 | 0.23 | 0.95 | 0.24 | 0.94 | 0.21 | 0.86 | 0.18 | 0.80 | 0.15 |
| | 0.95 | 0.30 | 0.96 | 0.38 | 0.96 | 0.44 | 0.89 | 0.23 | 0.84 | 0.21 |
| | 1.03 | 1.48 | 1.03 | 1.65 | 1.03 | 2.51 | 0.95 | 0.23 | 0.87 | 0.23 |
| | 1.05 | 0.16 | 1.10 | 0.22 | 1.05 | 0.31 | 0.96 | 0.48 | 0.94 | 0.19 |
| | 1.11 | 0.17 | 1.12 | 0.36 | 1.07 | 0.24 | 1.03 | 1.75 | 0.95 | 0.57 |
| | 1.14 | 0.15 | 1.13 | 0.41 | 1.11 | 0.26 | 1.05 | 0.36 | 0.97 | 0.15 |
| | 1.15 | 0.24 | 1.18 | 0.17 | 1.13 | 0.69 | 1.07 | 0.19 | 1.03 | 1.05 |
| | | | | | 1.15 | 0.53 | 1.11 | 0.23 | 1.04 | 2.06 |
| | | | | | 1.20 | 0.18 | 1.12 | 0.15 | 1.06 | 0.49 |
| | | | | | 1.26 | 0.26 | 1.13 | 0.74 | 1.08 | 0.26 |
| | | | | | | | 1.14 | 0.55 | 1.13 | 0.35 |
| | | | | | | | 1.16 | 0.16 | 1.15 | 0.93 |
| | | | | | | | 1.19 | 0.18 | 1.17 | 0.52 |
| | | | | | | | 1.25 | 0.16 | 1.21 | 0.19 |
| | | | | | | | 1.37 | 0.15 | 1.30 | 0.31 |
| | | | | | | | 1.48 | 0.16 | 1.44 | 0.22 |
| | | | | | | | | | 1.53 | 0.21 |
| | | | | | | | | | 1.56 | 0.21 |

ROSE-010 Pharmacokinetics in Rats

The PK profile of ROSE-010 administered as ROSE-010 TECHNOSPHERE® prototype powders was evaluated in female Sprague Dawley rats (n=10/group) by pulmonary insufflation and compared to ROSE-010 administered by intravenous (IV) and subcutaneous (SC) injection (Table 6).

TABLE 6

ROSE-010 PK study design.

| Group | Test Article | Dose (mg ROSE-010) | Route of Administration |
|---|---|---|---|
| 1 | ROSE-010 | 0.1 | IV |
| 2 | ROSE-010 | 0.1 | SC |
| 3 | ROSE-010 TECHNOSPHERE ® powder pH 4.5 | 0.1 | Insufflation |
| 4 | ROSE-010 TECHNOSPHERE ® powder pH 4.5 | 0.2 | Insufflation |
| 5 | ROSE-010 TECHNOSPHERE ® powder pH 4.5 | 0.3 | Insufflation |
| 6 | ROSE-010 TECHNOSPHERE ® powder pH 3 | 0.3 | Insufflation |

Figure 9:
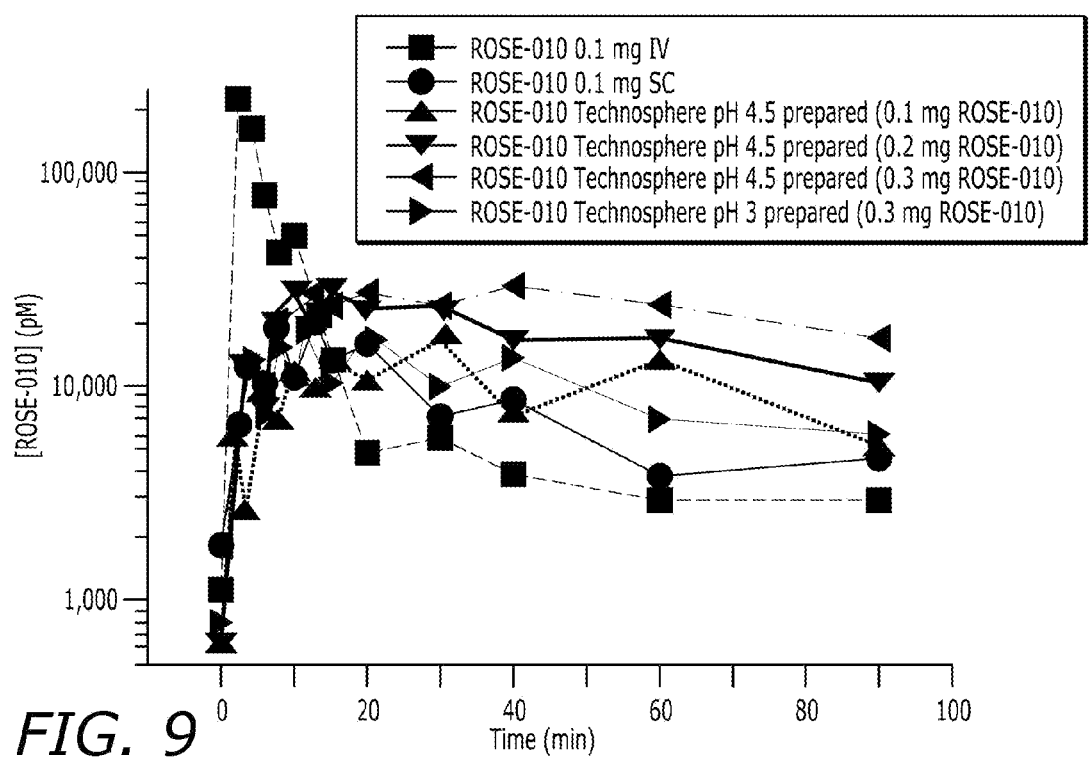
FIG. 9 depicts a graphic representation of the data obtained from pharmacodynamic studies comparing intravenous, subcutaneous and pulmonary administration of the GLP-1 analog ROSE-010 in plasma of rats for a period of time up to 90 minutes after administration.

Blood samples for ROSE-010 analysis were collected before dosing and at 2, 4, 6, 8, 10, 12, 15, 20, 30, 40, 60 and 90 minutes after dosing. ROSE-010 in plasma was analyzed using enzyme-linked immunosorbent assay (ELISA) against a GLP-1 standard (n=5 rats/time point). Subsequently, ROSE-010 was found to be significantly less sensitive than GLP-1 in the ELISA assay, so a conversion factor was used to correct for this difference. The PK profiles of ROSE-010 insufflated as ROSE-010 TECHNOSPHERE® powders were dose-related and comparable to ROSE-010 administered by subcutaneous injection. ROSE-010 administered by IV injection demonstrated a faster time to peak circulating concentrations (FIG. 9).

ROSE-010 was well tolerated across all treatment groups. Pharmacokinetic parameters corrected for administered dose were calculated using noncompartmental methods and the nonlinear regression program WinNonlin (Table 7) corrected for administered doses.

TABLE 7

ROSE-010 PK parameters.

| Group | Test Article (ROSE-010 dose in mg) | Half life (min) | $T_{max}$ (min) | $C_{max}$ (pM) | $AUC_{all}$ (min * pM) | $AUC_{all}$-D (min * pM/mg) | Bioavailability (%) |
|---|---|---|---|---|---|---|---|
| 1 | ROSE-010 (0.1) | 71 | 2 | 231,108 | 1,475,765 | 14,757,650 | 100 |
| 2 | ROSE-010 (0.1) | 35 | 8 | 20,314 | 708,706 | 7,087,064 | 48 |
| 3 | ROSE-010 TECHNOSPHERE ® (0.1) | 48 | 6 | 9,966 | 886,160 | 8,861,600 | 60 |
| 4 | ROSE-010 TECHNOSPHERE ® (0.2) | 59 | 10 | 25,760 | 1,543,529 | 7,717,645 | 52 |
| 5 | ROSE-010 TECHNOSPHERE ® (0.3) | 65 | 10 | 21,894 | 2,022,256 | 6,740,853 | 46 |
| 6 | ROSE-010 TECHNOSPHERE ® (0.3) | 47 | 8 | 15,179 | 871,523 | 2,905,077 | 20 |

*$T_{max}$ and $C_{max}$ were defined as the initial point in the concentration curve plateau.

Overall, ROSE-010 was systemically bioavailable following pulmonary insufflation with ROSE-010 TECHNOSPHERE® powder. Absolute ROSE-010 bioavailability was between 46 and 60% with powder prepared at pH 4.5; and 20% with powder prepared at pH 3. ROSE-010 was absorbed rapidly after pulmonary insufflation with Cmax occurring approximately 6 minutes after administration.

ROSE-010 Pharmacodynamics Results

ROSE-010 TECHNOSPHERE® powder was tested in the rat migrating myoelectric/motor complex (MMC) model and compared to intravenous or subcutaneous injection of ROSE-010. Animals received either ROSE-010 (0.03 mg) by IV or SC injection or ROSE-010 TECHNOSPHERE® powder (0.03 or 0.06 mg ROSE-010) by pulmonary insufflation.

Myoelectric activity was continuously recorded over 6-8 hours. The animals were fasted with a stable MMC pattern. After a control period of four MMC cycles, animals were briefly (~4 min) anesthetized with 3-4% isoflurane and rapidly insufflated with air or ROSE-010 TECHNOSPHERE® powder at doses of 0.06 and 0.03 mg ROSE-010. Alternatively 0.03 mg ROSE-010 was given IV or SC. Recording was continued until four MMC cycles were resumed.

Figure 10:
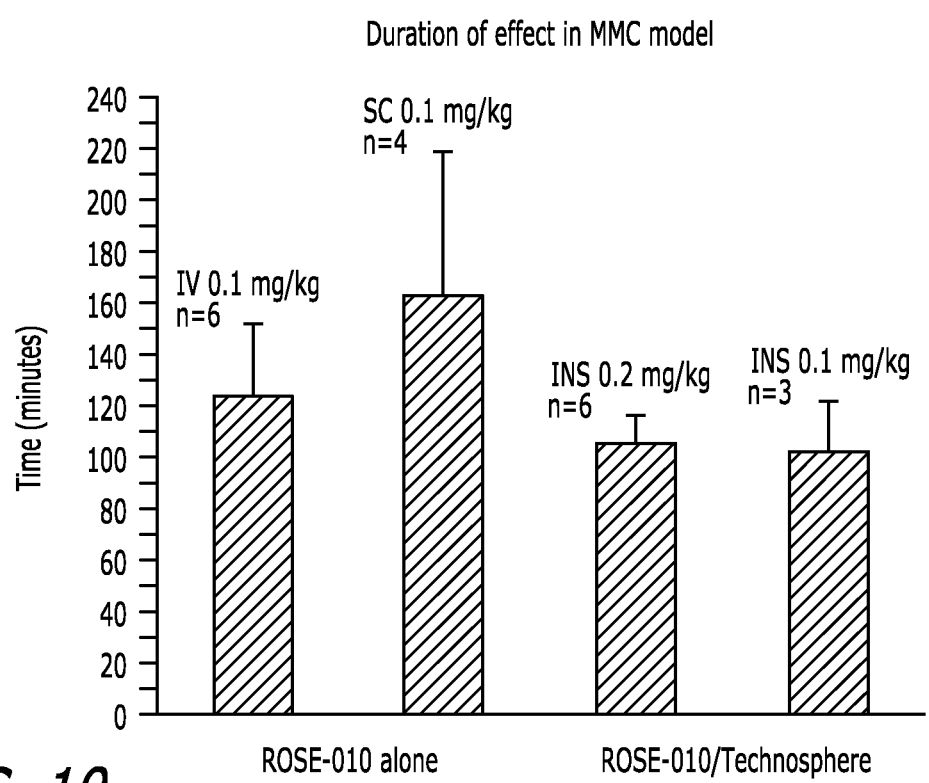
FIG. 10 depicts a bar graph showing the effects of FDKP-ROSE-010 on myotonic muscle contraction in the gastrointestinal tract of rats, which measures the duration of effect in MMC model. INS=insufflation.

Pulmonary insufflation of ROSE-010 TECHNOSPHERE® powder (0.06 mg ROSE-010) increased MMC cycle length from 18.7±7.3 to 105.9±9.5 min (n=6), and 0.03 mg ROSE-010 increased MMC cycle length from 19.4±2.9 to 102.6±18.3 min (n=3). IV or SC ROSE-010 (0.03 mg) prolonged the MMC cycle from 18.3±2.5 and 14.8±2.0 min to 124.1±27.3 and 148.1±49.4 min, respectively (n=6/group). There was no increase in MMC cycle length in animals administered air by insufflation (FIG. 10). This study demonstrated that MMC inhibition following pulmonary insufflation of ROSE-010 TECHNOSPHERE® powder is comparable to inhibition following intravenous or subcutaneous injection of ROSE-010 at similar doses.

FIG. 10 illustrates the duration of MMC suppression in male Sprague Dawley Rats administered ROSE-010 by intravenous injection or subcutaneous injection or ROSE-010 TECHNOSPHERE® powder by pulmonary insufflation.

The data indicate that the ROSE-010 TECHNOSPHERE® powder formulation administered to rats by the pulmonary route show measurable levels of ROSE-010 in blood. In these studies, ROSE-010 insufflated as a ROSE-010 TECHNOSPHERE® powder demonstrated dose dependent increases in exposure, bioavailability of 60% relative to IV injection (greater than SC administration), and inhibition of the MMC comparable to SC and IV administration. The data obtained demonstrate that pulmonary insufflation of ROSE-010 TECHNOSPHERE® powder (0.2 mg/kg ROSE-010) increased MMC cycle length from 18.7±7.3 to 105.9±9.5 min (n=6), and 0.1 mg/kg ROSE-010 from 19.4±2.9 to 102.6±18.3 min (n=3). IV or SC ROSE-010 (0.1 mg/kg) prolonged the MMC cycle from 18.3±2.5 and 14.8±2.0 min to 124.1±27.3 and 148.1±49.4 min, respectively (n=6/group). There was no increase in MMC cycle length in animals administered air by insufflation.

In summary, MMC inhibition following pulmonary insufflation of ROSE-010 TECHNOSPHERE® powder is comparable to inhibition following IV or SC injection of ROSE-010 at similar doses (p>0.05).

Example 3

Administration of GLP-1 in an Inhalable Dry Powder to Healthy Adult Males

GLP-1 has been shown to control elevated blood glucose in humans when given by intravenous (IV) or subcutaneous (SC) infusions or by multiple subcutaneous injections. Due to the extremely short half-life of the hormone, continuous subcutaneous infusion or multiple daily subcutaneous injections would be required to achieve clinical efficacy. Neither of these routes is practical for prolonged clinical use. Applicants have found in animal experiments that when GLP-1 was administered by inhalation, therapeutic levels could be achieved. The results of these studies can be found, for example, in U.S. patent application Ser. No. 11/735,957, the disclosure of which is incorporated by reference herein.

In healthy individuals, several of the actions of native GLP-1, including reduction in gastric emptying, increased satiety, and suppression of inappropriate glucagon secretion appear to be linked to the burst of GLP-1 released as meals begin. By supplementing this early surge in GLP-1 with a formulation of GLP-1 and 2,5-diketo-3,6-di(4-fumaryl-aminobutyl)piperazine (FDKP) as an inhalation powder, a pharmacodynamic response, including endogenous insulin production, reduction in glucagon and glucose levels, in diabetic animals can be elicited. In addition, the late surge in native GLP-1 linked to increased insulin secretion can be mimicked by postprandial administration of GLP-1/FDKP inhalation powder.

A Phase 1a clinical trials of GLP-1/FDKP inhalation powder was designed to test the safety and tolerability of selected doses of a new inhaled glycemic control therapeutic product for the first time in human subjects. GLP-1/FDKP inhalation powder was administered using the MEDTONE® Inhaler device, previously tested. The experiments were designed to identify the safety and tolerability of various doses of GLP-1/FDKP inhalation powder by pulmonary inhalation. Doses were selected for human use based on animal safety study results from non-clinical studies in rats and primates using GLP-1/FDKP administered by inhalation as described in U.S. application Ser. No. 11/735,957, which is incorporated herein by reference.

Twenty-six subjects were enrolled into 5 cohorts to provide up to 4 evaluable subjects in each of cohorts 1 and 2 and up to 6 evaluable subjects in each of cohorts 3 to 5 who met eligibility criteria and completed the study. Each subject was dosed once with GLP-1 as GLP-1/FDKP inhalation powder at the following dose levels: cohort 1: 0.05 mg; cohort 2: 0.45 mg; cohort 3: 0.75 mg; cohort 4: 1.05 mg and cohort 5: 1.5 mg of GLP-1. Dropouts were not replaced. These dosages assumed a body mass of 70 kg. Persons of ordinary skill in the art can determine additional dosage levels based on the studies disclosed herein.

In these experiments, the safety and tolerability of ascending doses of GLP-1/FDKP inhalation powder in healthy adult male subjects were determined. The tolerability of ascending doses of GLP-1/FDKP inhalation powder were determined by monitoring pharmacological or adverse effects on variables including reported adverse events (AE), vital signs, physical examinations, clinical laboratory tests and electrocardiograms (ECG).

Additional pulmonary safety and pharmacokinetic parameters were also evaluated. Pulmonary safety as expressed by the incidence of pulmonary and other adverse events and changes in pulmonary function between Visit 1 (Screening) and Visit 3 (Follow-up) was studied. Pharmacokinetic (PK) parameters of plasma GLP-1 and serum FDKP following dosing with GLP-1/FDKP inhalation powder were measured as $AUC_{0-120\ min}$ plasma GLP-1 and $AUC_{0-480\ min}$ serum FDKP. Additional PK parameters of plasma GLP-1 included the time to reach maximal plasma GLP-1 concentration, $T_{max}$ plasma GLP-1; the maximal concentration of GLP-1 in plasma, $C_{max}$ plasma GLP-1, and the half of total time to reach maximal concentration of GLP-1 in plasma, $T_{1/2}$ plasma GLP-1. Additional PK parameters of serum FDKP included $T_{max}$ serum FDKP, $C_{max}$ serum FDKP, and $T_{1/2}$ serum FDKP. Clinical trial endpoints were based on a comparison of the following pharmacological and safety parameters determined in the trial subject population. Primary endpoints included the incidence and severity of reported AEs, including cough and dyspnea, nausea and/or vomiting, as well as changes from screening in vital signs, clinical laboratory tests and physical examinations. Secondary endpoints included pharmacokinetic disposition of plasma GLP-1 and serum FDKP ($AUC_{0-120\ min}$ plasma GLP-1 and $AUC_{0-480\ min}$ serum FDKP), plasma GLP-1 ($T_{max}$ plasma GLP-1, $C_{max}$ plasma GLP-1 $T_{1/2}$ plasma GLP-1); serum FDKP ($T_{max}$ serum FDKP, $C_{max}$ serum FDKP); pulmonary function tests (PFTs), and ECG.

The clinical trial consisted of 3 clinic visits: 1) One screening visit (Visit 1); 2) One treatment visit (Visit 2); and 3) One follow-up visit (Visit 3) 8-14 days after Visit 2. A single dose of GLP-1/FDKP inhalation powder was administered at Visit 2.

Five doses of GLP-1/FDKP inhalation powder (0.05, 0.45, 0.75, 1.05 and 1.5 mg of GLP-1) were assessed. To accommodate all doses, formulated GLP-1/FDKP was mixed with FDKP inhalation powder containing particles without active agent. Single-dose cartridges containing 10 mg dry powder consisting of GLP-1/FDKP inhalation powder (15% weight to weight GLP-1/FDKP) as is or mixed with the appropriate amount of FDKP inhalation powder was used to obtain the desired dose of GLP-1 (0.05 mg, 0.45 mg, 0.75 mg, 1.05 mg and 1.5 mg). The first 2 lowest dose levels were evaluated in 2 cohorts of 4 subjects each and the 3 higher dose levels were evaluated in 3 cohorts of 6 subjects each. Each subject received only 1 dose at 1 of the 5 dose levels assessed. In addition to blood drawn for GLP-1 (active and total) and FDKP measurements, samples were drawn for glucagon, glucose, insulin, and C-peptide determination. The results from these experiments are described with reference to the following figures and tables.

Figure 11:
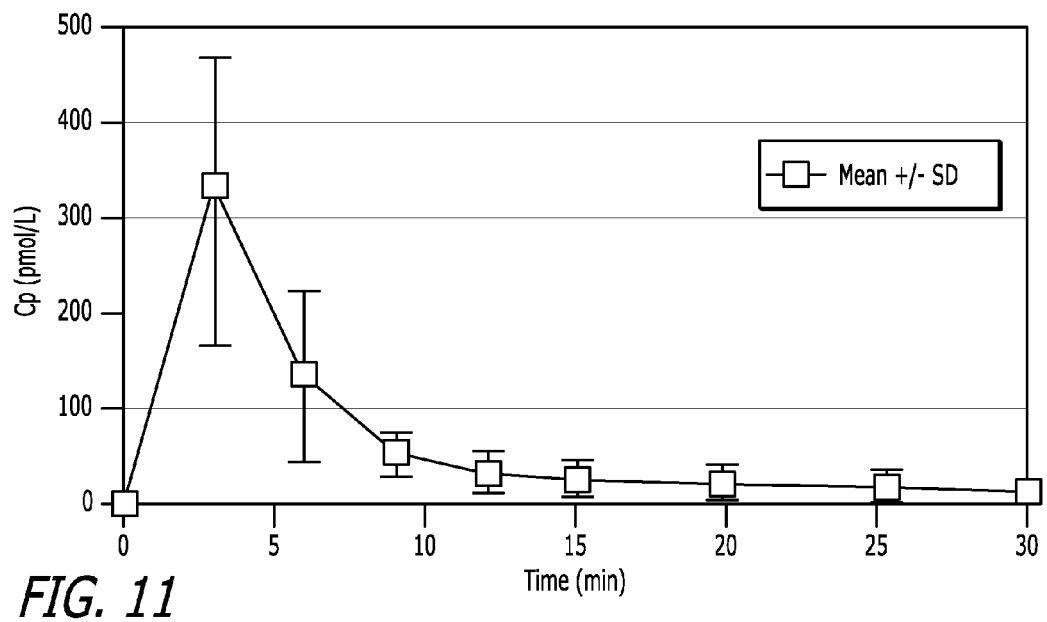
FIG. 11 depicts the mean plasma concentration of active and native GLP-1 in subjects treated with an inhalable dry powder formulation containing a GLP-1 dose of 1.5 mg measured at various times after inhalation.

FIG. 11 depicts the active GLP-1 plasma concentration in cohort 5 after pulmonary administration of 1.5 mg of GLP-1 dose. The data showed that the peak GLP-1 concentration occurred prior to the first sampling point at 3 min, closely resembling IV bolus administration. GLP-1 plasma concentrations in some subjects were greater than 500 pmol/L, the assay limit. Peak active GLP-1 plasma concentrations range from about 150 pmol/L to about 500 pmol/L. Intravenous bolus administration of GLP-1 as reported in the literature (Vilsboll et al. 2000) results in ratios of total:active GLP-1 of 3.0-5.0 compared to a ratio of 1.5 in cohort 5 of this study. At comparable active concentrations the metabolite peaks were 8-9 fold greater following intravenous administration compared to pulmonary administration, suggesting that pulmonary delivery results in rapid delivery and less degradation of GLP-1.

TABLE 8

| Parameter[a] | Treatment | | | | |
|---|---|---|---|---|---|
| | 0.05 mg (n = 4) | 0.45 mg (n = 4) | 0.75 mg (n = 6) | 1.05 mg (n = 6) | 1.5 mg (n = 6) |
| | GLP-1[a] | | | | |
| $AUC_{0-120}$ (min*pmol/L) | ND | n = 1 355.33 | n = 6 880.12 (195.656) | n = 4 1377.88 (634.054) | n = 4 AULQ |
| $C_{max}$ (pmol/L) | n = 4 2.828 (2.4507) | n = 4 24.630 (8.7291) | n = 6 81.172 (63.3601) | n = 6 147.613 (122.7014) | n = 6 310.700 (54.2431) |
| $t_{max}$ (min) | n = 4 3.00 (3.00, 3.00) | n = 4 3.00 (3.00, 4.02) | n = 6 3.00 (3.00, 6.00) | n = 6 3.00 (3.00, 4.98) | n = 6 3.00 (3.00, 3.00) |

TABLE 8-continued

| Parameter[a] | Treatment | | | | |
|---|---|---|---|---|---|
| | 0.05 mg (n = 4) | 0.45 mg (n = 4) | 0.75 mg (n = 6) | 1.05 mg (n = 6) | 1.5 mg (n = 6) |
| $T_{1/2}$ (min) | n = 1 6.1507 | n = 3 3.0018 (0.83511) | n = 6 5.5000 (2.96928) | n = 4 3.6489 (1.88281) | n = 6 3.9410 (1.79028) |
| FDKP | | | | | |
| $AUC_{0-120}$ (min*pmol/L) | | | | n = 6 22169.2 (4766.858) | n = 6 25594.7 (5923.689) |
| $C_{max}$ (pmol/L) | | | | n = 6 184.21 (56.893) | n = 6 210.36 (53.832) |
| $t_{max}$ (min) | | | | n = 6 4.50 (3.00, 25.02) | n = 6 6.00 (3.00, 19.98) |
| $T_{1/2}$ (min) | | | | n = 6 126.71 (11.578) | n = 6 123.82 (15.640) |

[a]All parameters are mean (SD) except tmax, which is median (range)
AULQ—Two or more subjects in the dose group had plasma concentrations of the analyte that were AULQ;
NA = The pharmacokinetic profile did not meet the specifications for this profile because of the short sampling time (20 minutes);
ND = Parameter could not be calculated because of insufficient data is some subjects.

In healthy individuals, physiological post-prandial venous plasma concentrations of GLP-1 typically range from 10-20 pmol/L (Vilsboll et al. *J. Clin. Endocr. & Metabolism.* 88(6): 2706-13, June 2003). These levels were achieved with some subjects in cohort 2, who received 0.45 mg GLP-1. Higher doses of GLP-1 produced peak plasma GLP-1 concentrations substantially higher than physiological peak venous concentrations. However, because the half-life of GLP-1 is short (about 1-2 min), plasma concentrations of active GLP-1 fell to the physiological range by 9 min after administration. Although the peak concentrations are much higher than those seen physiologically in the venous circulation, there is evidence that local concentrations of GLP-1 may be much higher than those seen systemically.

Table 8 shows the pharmacokinetic profile of GLP-1 in a formulation comprising FDKP from this study.

FDKP pharmacokinetic parameters are also represented in Table 8 for cohorts 4 and 5. Other cohorts were not analyzed. The data also shows that mean plasma concentration of FDKP for the 1.05 mg and the 1.5 mg GLP-1 treated subjects were about 184 and 211 pmol/L, respectively. Maximal plasma FDKP concentrations were attained at about 4.5 and 6 min after administration for the respective dose with a half-life about 2 hr (127 and 123 min).

Figure 12:
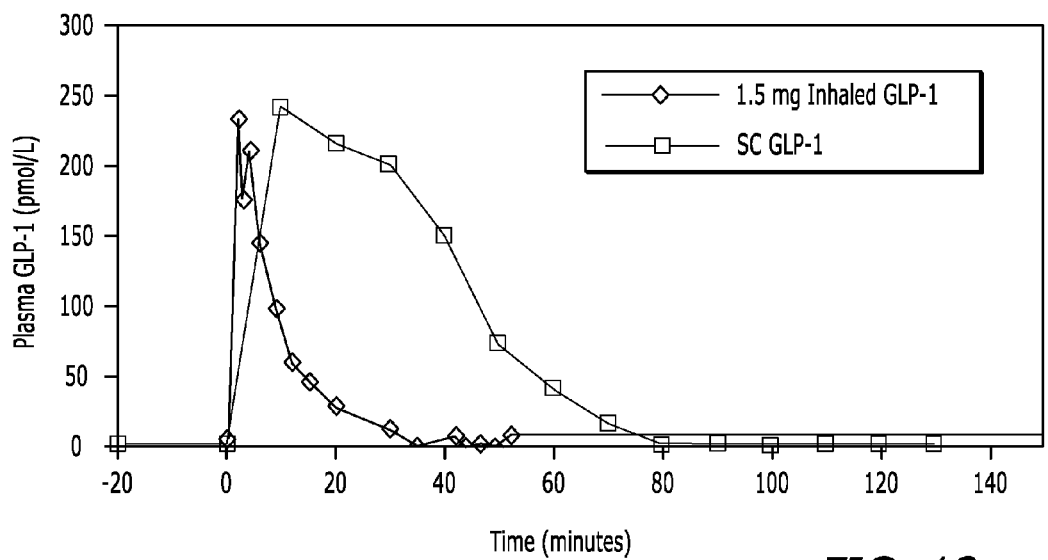
FIG. 12 depicts the plasma concentration of GLP-1 in subjects treated with an inhalable dry powder formulation containing a GLP-1 dose of 1.5 mg measured at various times after inhalation compared to subjects treated with a subcutaneous administration of GLP-1.

FIG. 12 depicts the GLP-1 plasma concentration of subjects treated with the 1.5 mg dose of GLP-1 administered by pulmonary inhalation compared to subcutaneous administration of a GLP-1 dose. The data illustrates that pulmonary administration of GLP-1 occurs relatively fast and peak plasma concentration of GLP-1 occur faster than with subcutaneous administration. Additionally, pulmonary inhalation of GLP-1 leads to GLP-1 plasma concentrations returning to basal levels much faster than with subcutaneous administration. Thus the exposure of the patient to GLP-1 provided by pulmonary inhalation using the present drug delivery system is shorter in time than by subcutaneous administration and the total exposure to GLP-1 as measured by AUC is less for the inhaled insulin.

Tables 9 and 10 report the adverse events or side effect symptoms recorded for the patient population in the study. The list of adverse events reported in the literature for GLP-1 administered by injection is not extensive; and those reported have been described as mild or moderate, and tolerable. The primary adverse events reported have been profuse sweating, nausea and vomiting when active GLP-1 concentrations exceed 100 pmol/L. As shown in Tables 8 and 10, and FIG. 12, pulmonary administration at doses of 1.05 mg and 1.5 mg resulted in active GLP-1 concentrations greatly exceeding 100 pmol/L without the side effects normally observed with parenteral (subcutaneous, intravenous [either bolus or infusion]) GLP-1. None of the subjects in this study reported symptoms of nausea, profuse sweating or vomiting. Subjects in Cohort 5 reached $C_{max}$ comparable to that observed with a 50 μg/kg IV bolus data (reported by Vilsboll et al. 2000), where the majority of subjects reported significant adverse events.

TABLE 9

Adverse Events

| Adverse Event | 0.05 mg (n = 4) | 0.45 mg (n = 4) | 0.75 mg (n = 6) | 1.05 mg (n = 6) | 1.5 mg (n = 6) |
|---|---|---|---|---|---|
| Cough | 3 | 1 | 3 | 5 | 5 |
| Dysphonia | 2 | — | 2 | 3 | 3 |
| Productive Cough | — | — | 1 | — | — |
| Throat Irritation | — | — | — | 1 | — |
| Headache | 1 | 1 | — | 1 | 1 |
| Dizziness | — | — | — | — | 2 |
| Dysgeusia | — | — | 1 | — | — |
| Fatigue | — | — | 1 | 1 | 1 |
| Seasonal Allergy | — | — | — | 1 | — |
| Rhinitis | — | — | — | 1 | — |
| Increased Appetite | — | — | — | — | 1 |

TABLE 10

Comparative Adverse Events of GLP-1:
IV vs. Pulmonary Administration

| Adverse Events | IV† (16.7 μg) | IV†* (50 μg) | Pulmonary* (1.5 mg) |
|---|---|---|---|
| Reduced well-being | 42% | 100% | 17% |
| Nausea | 33% | 83% | 0% |
| Profuse sweating | 17% | 67% | 0% |

†Vilsboll et al. Diabetes Care, June 2000;
*Comparable $C_{max}$

Tables 9 and 10 show there were no serious or severe adverse events reported by any subjects in the study who received GLP-1 by pulmonary inhalation. The most commonly reported adverse events were those associated with inhalation of a dry powder, cough and throat irritation. Surprisingly, in the patients treated by pulmonary inhalation, no subject reported nausea or dysphoria, and there was no vomiting associated with any of these subjects. The inventors also found that pulmonary administration of GLP-1 in a dry powder formulation lack inhibition of gastric emptying in the above subjects (data not shown). Inhibition of gastric emptying is a commonly encountered unwanted side effect associated with injected standard formulations of GLP-1.

In summary, the clinical GLP-1/FDKP powder contained up to 15 wt % GLP-1 providing a maximum dose of 1.5 mg GLP-1 in 10 mg of powder. Andersen cascade measurements indicated that 35-70% of the particles had aerodynamic diameters <5.8 μm. A dose of 1.5 mg GLP-1 produced mean peak concentrations >300 pmol/L of active GLP-1 at the first sampling time (3 min); resulted in mean peak insulin concentrations of 375 pmol/L at the first measured time point (6 min); reduced mean fasting plasma glucose from 85 to 70 mg/dL 20 min after dosing; and was well tolerated and did not cause nausea or vomiting.

The data above are representative illustrations of the distribution of GLP-1 to specific tissues of the body after degradation of GLP-1 by endogenous enzymes. Based on the above determinations, the amounts of GLP-1 in brain and liver after pulmonary administration are about 1.82 to about 1.86 times higher than the amounts of GLP-1 after intravenous bolus administration. Therefore, the data indicate that pulmonary delivery of GLP-1 can be a more effective route of delivery when compared to intravenous administration of GLP-1, as the amount of GLP-1 at various times after administration would be about double the amount obtained with intravenous administration. Therefore, treatment of a disease or disorder comprising GLP-1 by pulmonary administration would require smaller total amounts, or almost half of an intravenous GLP-1 dose that is required to yield the same or similar effects.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A dry powder pharmaceutical composition comprising Val (8) glucagon-like peptide-1 (GLP-1) and a diketopiperazine or a pharmaceutically acceptable salt, solvate or prodrug thereof.

2. The composition of claim 1, wherein said diketopiperazine is a diketopiperazine having the formula 2,5-diketo-3,6-di(4-X-aminobutyl)piperazine, wherein X is selected from the group consisting of succinyl, glutaryl, maleyl, fumaryl, malonyl, oxalyl and citraconyl.

3. The composition of claim 1, wherein said diketopiperazine comprises a diketopiperazine salt.

4. The composition of claim 2, wherein said diketopiperazine is 2,5-diketo-3,6-di(4-fumaryl-aminobutyl)piperazine.

5. The composition of claim 1, wherein said Val (8) GLP-1 is an amidated Val (8) GLP-1.

6. A process for forming a dry powder of claim 1 comprising:
removing a solvent from a co-solution of a Val (8) GLP-1 and a particle-forming diketopiperazine, diketopiperazine particles, or a combination thereof.

7. The process of claim 6, wherein the solvent is removed from said co-solution by lyophilization, filtration, or spray drying.

8. The process of claim 7, wherein said particles comprising said Val (8) GLP-1 and said diketopiperazine are formed by removing said solvent by spray drying.

9. The process of claim 7, wherein said particles comprising said Val (8) GLP-1 and said diketopiperazine are formed prior to removing said solvent.

10. The process of claim 6, wherein said Val (8) GLP-1 is provided in the form of a solution comprising a Val (8) GLP-1 concentration of about 0.001 mg/ml -50 mg/ml.

11. The process of claim 10, wherein said Val (8) GLP-1 is provided in the form of a solution comprising a Val (8) GLP-1 concentration of about 0.1 mg/ml -10 mg/ml.

12. The process of claim 10, wherein said Val (8) GLP-1 is provided in the form of a solution comprising a Val (8) GLP-1 concentration of about 0.25 mg/ml.

13. The process of claim 6, wherein said diketopiperazine is provided in the form of a suspension of diketopiperazine particles.

14. The process of claim 13, further comprising adding an agent to said suspension, wherein the agent is selected from the group consisting of salts, surfactants, ions, osmolytes, chaotropes and lyotropes, acids, bases, and organic solvents.

15. The process of claim 14 wherein said agent promotes association between said Val (8) GLP-1 and said diketopiperazine particles.

16. The process of claim 15, wherein said agent is sodium chloride.

17. A method of administering an effective amount of a Val(8) GLP-1 to a subject in need thereof comprising administering a dry powder of claim 1 by pulmonary delivery.

18. The method of claim 17, wherein said pulmonary delivery is obtained using a dry powder inhalation system.

19. The method of claim 17, wherein the dry powder inhalation system comprises a cartridge.

* * * * *

UNITED STATES PATENT AND TRADEMARK OFFICE
CERTIFICATE OF CORRECTION

| | | |
|---|---|---|
| PATENT NO. | : 8,642,548 B2 | Page 1 of 1 |
| APPLICATION NO. | : 13/389410 | |
| DATED | : February 4, 2014 | |
| INVENTOR(S) | : Peter Richardson et al. | |

It is certified that error appears in the above-identified patent and that said Letters Patent is hereby corrected as shown below:

Title Page, (73) Assignee should appear as follows:
MANNKIND CORPORATION, VALENCIA, CA (US)
ROSE PHARMA A/S, COPENHAGEN, DENMARK Signed and Sealed this
Fifth Day of August, 2014

Michelle K. Lee
*Deputy Director of the United States Patent and Trademark Office*